(12) United States Patent  (10) Patent No.: US 8,529,803 B2
Fujie et al.  (45) Date of Patent: Sep. 10, 2013

(54) CURABLE COLORING COMPOSITION, COLOR FILTER AND METHOD FOR PRODUCING SAME, AND QUINOPHTHALONE DYE

(75) Inventors: Yoshihiko Fujie, Shizuoka (JP); Yuuki Mizukawa, Shizuoka (JP); Shinichi Kanna, Shizuoka (JP); Kazuya Oota, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/260,118

(22) PCT Filed: Mar. 19, 2010

(86) PCT No.: PCT/JP2010/054785
§ 371 (c)(1),
(2), (4) Date: Dec. 19, 2011

(87) PCT Pub. No.: WO2010/110199
PCT Pub. Date: Sep. 30, 2010

(65) Prior Publication Data
US 2012/0112142 A1  May 10, 2012

(30) Foreign Application Priority Data

Mar. 26, 2009  (JP) ................. 2009-076521

(51) Int. Cl.
*G02B 5/23* (2006.01)
*G03C 1/00* (2006.01)
*G03F 7/00* (2006.01)
*C09B 25/00* (2006.01)

(52) U.S. Cl.
USPC ......... 252/586; 430/7; 430/270.1; 430/285.1; 430/321; 546/154

(58) Field of Classification Search
USPC ............... 252/586; 430/7, 270.1, 285.1, 321; 546/154
See application file for complete search history.

(56) References Cited

FOREIGN PATENT DOCUMENTS

| JP | 50-107279 A | 8/1975 |
|---|---|---|
| JP | 7-111485 B2 | 5/1990 |

(Continued)

*Primary Examiner* — Bijan Ahvazi
(74) *Attorney, Agent, or Firm* — Sughrue Mion, PLLC

(57) ABSTRACT

A curable coloring composition includes a quinophthalone dye of Formula (1). A color filter employing the composition, a method for producing the color filter, and a quinophthalone dye of Formula (2) are also described. The curable coloring composition and color filter have good color hue, high transmittance properties, high light fastness and heat fastness, and excellent stability over time and solvent resistance.

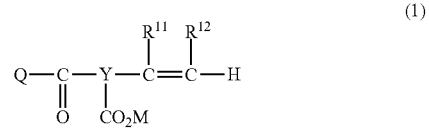

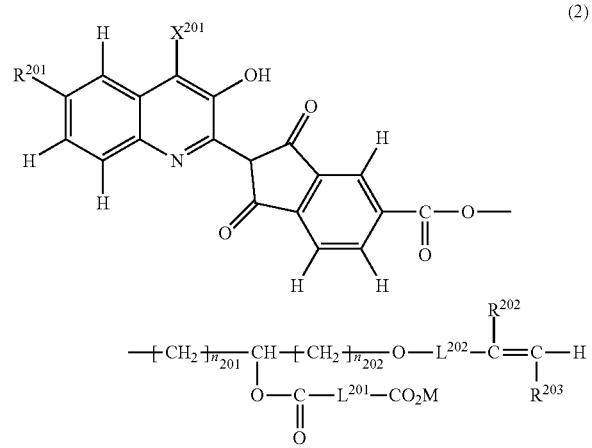

12 Claims, 2 Drawing Sheets

(56) References Cited

FOREIGN PATENT DOCUMENTS

| | | |
|---|---|---|
| JP | 05-271567 A | 10/1993 |
| JP | 06-075375 A | 3/1994 |
| JP | 2002-014221 A | 1/2002 |
| JP | 2002-014223 A | 1/2002 |
| JP | 2006-091768 A | 4/2006 |
| JP | 2007-147784 A | 6/2007 |

CURABLE COLORING COMPOSITION, COLOR FILTER AND METHOD FOR PRODUCING SAME, AND QUINOPHTHALONE DYE

CROSS REFERENCE TO RELATED APPLICATIONS

This is a National Stage of International Application No. PCT/JP2010/054785 filed Mar. 19, 2010, claiming priority based on Japanese Patent Application No. 2009-076521 filed Mar. 26, 2009, the contents of all of which are incorporated herein by reference in their entirety.

TECHNICAL FIELD

The present invention relates to a curable coloring composition that is suitable for forming a color filter used in a liquid crystal display (LCD) or a solid-state image sensor (e.g. CCD, CMOS, etc.), a color filter employing the curable coloring composition and a method for producing same, and a quinophthalone dye having a specific structure.

BACKGROUND ART

As a color filter formed above a device in order to color a solid-state image sensor or a liquid crystal display, a color filter formed from a yellow filter layer, a magenta filter layer, and a cyan filter layer that are formed adjacent to each other on the same plane above a substrate, or a color filter formed from a red filter layer, a green filter layer, and a blue filter layer are known. In these filter layers, a band-shaped pattern or a mosaic pattern is formed.

As a method for producing the above-mentioned color filter, various methods have been proposed. Among them, a so-called color resist method, in which a step of carrying out patterning by exposing and developing a dye-containing photosensitive resin composition is repeated a required number of times, has been widely put into practice.

The color resist method is a method for producing a color filter by a photolithographic method using a colored radiation-sensitive composition in which a pigment is dispersed in various photosensitive compositions; this method is considered to be a method suitable for production of a color filter for a large screen, high resolution color display since it is stable to light, heat, etc. due to a pigment being used and the positional precision is sufficient due to patterning being carried out by a photolithographic method.

When a color filter is produced as described above by a pigment dispersion method in which a pigment is dispersed, a color filter is obtained by forming a coating by coating a glass substrate with a radiation-sensitive composition using a spin coater, a roll coater, etc., carrying out pattern exposure and developing of this coating so as to obtain colored pixels, and carrying out this procedure for the number of hues required. As the pigment dispersion method, a negative-working photosensitive composition in which a photopolymerizable monomer and a photopolymerization initiator are used for an alkali-soluble resin has been disclosed (ref. e.g. Patent Documents 4 and 5).

On the other hand, in recent years, higher resolution has been desired for a color filter for a solid-state image sensor. However, in the above-mentioned conventional pigment dispersion system, the resolution does not improve, there is the problem that color unevenness occurs due to coarse pigment particles, etc., and it is therefore not suitable for application where a fine pattern is required as for a solid-state image sensor. In order to solve such a problem, the use of a dye has been proposed in the art (ref. e.g. Patent Documents 1 and 2). Furthermore, a positive-working photosensitive composition has also been disclosed (ref. e.g. Patent Documents 3 and 4).

Moreover, Patent Document 6 discloses a colorant-containing curable composition formed from a colorant, the colorant comprising a compound represented by Formula (1) below and/or a tautomer thereof.

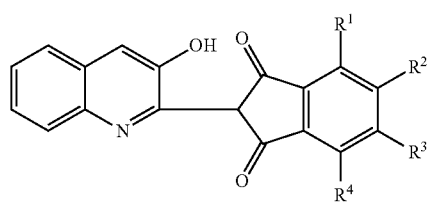

Formula (1)

(In Formula (1), $R^1$ to $R^4$ independently denote a hydrogen atom, a halogen atom, —S—$R^5$, or —S—$R^6$. S denotes a sulfur atom, and $R^5$ denotes an alkyl group containing an oxygen atom in the form of an ether bond and may further have a hydroxy group as a substituent. $R^6$ denotes an alkyl group having a hydroxy group. At least one of $R^1$ to $R^4$ denotes —S—$R^5$.)

Patent Document 7 discloses a curable coloring composition comprising a polymer dye, the polymer dye being at least one type selected from the group consisting of a copolymer of at least one type of dye monomer represented by Formula (P) below and at least one type of colorless monomer having at least one ethylenic double bond and a polymer derived from at least one type of dye monomer represented by Formula (P) below.

$$Q-(L^1)_i-\overset{R^{a1}}{\underset{|}{C}}=CH-R^{a2}$$

Formula (P)

(In Formula (P), $R^{a1}$ and $R^{a2}$ mutually independently denote a hydrogen atom, an aliphatic group, an aryl group, or a heterocyclic group, $L^1$ denotes any one of (L-1), (L-2), (L-3), and (L-4) below, and i denotes 0 or 1. Q denotes a dye residue that is formed by removing a hydrogen atom from any possible position of a dye represented by Formula (1) below.)

$$-\underset{\underset{O}{\|}}{\overset{R^{a3}}{\underset{|}{C}N}}-$$

(L-1)

$$-\underset{\underset{O}{\|}}{CO}-$$

(L-2)

$$-\underset{\underset{|}{SO_2N}}{\overset{R^{a4}}{\underset{|}{}}}-$$

(L-3)

$$-SO_2-$$

(L-4)

(In (L-1) to (L-4), $R^{a3}$ and $R^{a4}$ mutually independently denote a hydrogen atom, an aliphatic group, an aryl group, or a heterocyclic group. In (L-1) to (L-4), the group having a dye residue and an ethylenic double bond may be bonded to either side.)

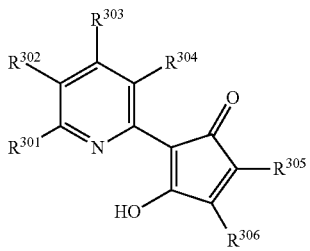

Formula (1)

(In Formula (1), $R^{301}$ to $R^{306}$ mutually independently denote a hydrogen atom or a substituent. When at least two of $R^{301}$ to $R^{306}$ are at adjacent positions, they may be bonded to each other to form a 5- to 6-membered ring, and the ring may further have a substituent.)

PRIOR ART DOCUMENTS

Patent Documents
Patent Document 1: JP-A-6-75375 (JP-A denotes a Japanese unexamined patent application publication)
Patent Document 2: JP-A-2002-14221
Patent Document 3: JP-B-7-111485 (JP-B denotes a Japanese examined patent application publication)
Patent Document 4: JP-A-2002-14223
Patent Document 5: JP-A-5-271567
Patent Document 6: JP-A-2006-91768
Patent Document 7: JP-A-2007-147784

SUMMARY OF THE INVENTION

Problems to be Solved by the Invention

However, the dye-containing curable coloring composition has the problems below, and further improvement is desired. That is,
(1) a dye is generally inferior to a pigment in terms of heat fastness, light fastness, etc.
(2) When the molar extinction coefficient of a dye is low, it is necessary to add a large amount of dye, and it is inevitable that there is a relative reduction in other components such as a polymerizable compound, a binder, and a photopolymerization initiator in the curable coloring composition. As a result, the heat fastness of a cured part that has been cured and the solvent resistance when a subsequent layer is applied are insufficient.
(3) Even when a dye has a high molar extinction coefficient, it is necessary to increase the molecular weight in order to improve the solubility in a liquid preparation of a dye that has poor solubility or improve the stability of a liquid preparation. As a result, it is necessary to add a large amount (weight) of dye, and it is inevitable that there is a relative reduction in other components such as a polymerizable compound, a binder, and a photopolymerization initiator in the curable coloring composition. Therefore, the heat fastness of a cured part that has been cured and the solvent resistance when a subsequent layer is applied are insufficient.

In order to improve the problems of the above-mentioned (2) and (3), a quinophthalone dye having a specific substituent has been examined (ref. e.g. Patent Documents 6 and 7). However, accompanying a recent desire for a thinner layer of color filters, it is inevitable that there is a relative reduction in other components such as a polymerizable compound, a binder, and a photopolymerization initiator in the curable coloring composition, the dye proposed here does not give sufficiently improved effects, and improvement is desired.

Furthermore, in order to improve the problems of the above-mentioned (2) and (3), a polymer dye of a quinophthalone dye has been examined (Patent Document 7). However, in terms of high resolution of a pattern in recent color filters, the proposed polymer dye is not sufficient, and further improvement is desired.

As described above, a dye that satisfies light and heat fastness, has good solubility, has excellent stability over time when preparing a curable coloring composition, sufficiently satisfies solvent resistance after curing, and is compatible with high resolution has not yet been found, and further improvement is desired.

Furthermore, in applications such as a solid-state image sensor where high resolution and uniform color in particular are required, a dye-containing curable coloring composition is useful, but it is necessary to improve the light and heat fastness and the stability over time of a liquid preparation. Moreover, when an organic solvent-soluble dye is used, since the organic solvent resistance of a colored pattern is not sufficient, if a subsequent color is applied over an existing pattern, the dye in the existing colored pattern leaches out, and there is a desire for improvement of such solvent resistance.

The present invention has been achieved in light of the above-mentioned circumstances, and it is an object thereof to provide a curable coloring composition that has good color hue, high transmittance properties, high light fastness and heat fastness, and excellent stability over time and solvent resistance after curing, a color filter that has good color hue, high transmittance properties, and excellent light fastness, heat fastness, and solvent resistance, and is compatible with high resolution, and a method for producing same.

Means for Solving the Problems

As a result of an intensive investigation the present inventors have succeeded in obtaining the finding that, in accordance with the use of a quinophthalone dye having a specific functional group, the light fastness and heat fastness increase, the stability over time is excellent, and the solvent resistance is improved, and the present invention has been accomplished based on such a finding.

Specific means for attaining the object are as follows.
<1> A curable coloring composition comprising at least one type of quinophthalone dye represented by Formula (1) below,

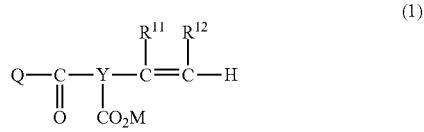

(1)

(In Formula (1), $R^{11}$ and $R^{12}$ mutually independently denote a hydrogen atom, a substituted or unsubstituted alkyl group, or a substituted or unsubstituted aryl group, M denotes a hydrogen atom, lithium, sodium, potassium, or an ammonium, Y denotes a trivalent linking group represented by (Y-1)

or (Y-2) below, and Q denotes a dye residue formed by removing one hydrogen atom from any possible position of a dye represented by Formula (Q) below.)

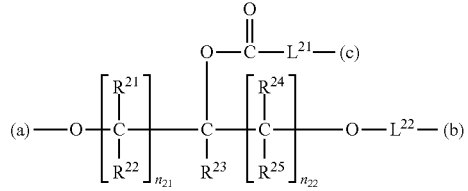
(Y-1)

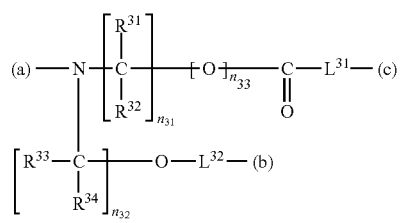
(Y-2)

(In (Y-1) and (Y-2), $R^{21}, R^{22}, R^{23}, R^{24}, R^{25}, R^{31}, R^{32}, R^{33}$, and $R^{34}$ mutually independently denote a hydrogen atom, a substituted or unsubstituted alkyl group, a substituted or unsubstituted aryl group, or a substituted or unsubstituted heterocyclic group, $n_1$ and $n_{22}$ mutually independently denote an integer of 0 to 3, $n_{31}$ and $n_{32}$ mutually independently denote an integer of 1 to 6, $n_{33}$ denotes an integer of 0 or 1, $L^{21}$ and $L^{31}$ denote a divalent linking group selected from the group consisting of (L-1) to (L-4) below, $L^{22}$ and $L^{32}$ denote a single bond or a divalent linking group selected from the group consisting of (L-4) to (L-7) below, (a) denotes a linking site to a carbonyl group bonded to dye residue (Q), (b) denotes a linking site to an ethylenically unsaturated group ($CR^{11}=CHR^{12}$), and (c) denotes a linking site to a carboxyl group ($CO_2M$).)

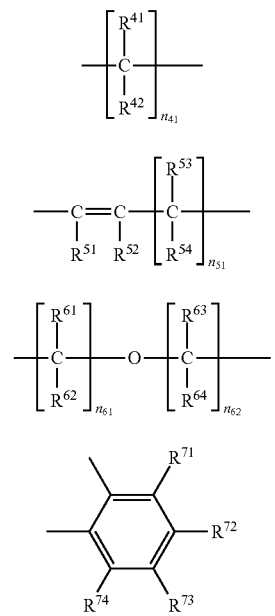
(L-1)
(L-2)
(L-3)
(L-4)

(L-5)
(L-6)

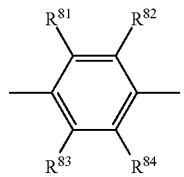
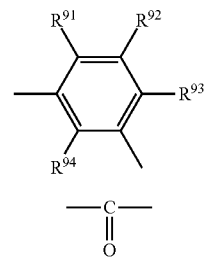

(L-7)

(In (L-1) to (L-7), $n_{41}$, $n_{51}$, $n_{61}$ and $n_{62}$ mutually independently denote an integer of 1 to 3, and $R^{41}, R^{42}, R^{51}, R^{52}, R^{53}, R^{54}, R^{61}, R^{62}, R^{63}, R^{64}, R^{71}, R^{72}, R^{73}, R^{74}, R^{81}, R^{82}, R^{83}, R^{84}, R^{91}, R^{92}, R^{93}$, and $R^{94}$ mutually independently denote a hydrogen atom or a monovalent substituent. When at least two of $R^{41}, R^{42}, R^{51}, R^{52}, R^{53}, R^{54}, R^{61}, R^{62}, R^{63}, R^{64}, R^{71}, R^{72}, R^{73}, R^{74}, R^{81}, R^{82}, R^{83}, R^{84}, R^{91}, R^{92}, R^{93}$, and $R^{94}$ are on the same carbon or at adjacent positions, they may be bonded to each other to form a 5- to 6-membered ring, and the ring may further have a substituent. In (L-1) to (L-4), a residue formed by removing $L^{21}$ from (Y-1) or a residue formed by removing $L^{31}$ from (Y-2) and a carboxyl group ($CO_2M$) may be bonded to either side, and in (L-4) to (L-7), a residue formed by removing $L^{22}$ from (Y-1) or a residue formed by removing $L^{32}$ from (Y-2) and an ethylenically unsaturated group ($CR^{11}=CHR^{12}$) may be bonded to either side.)

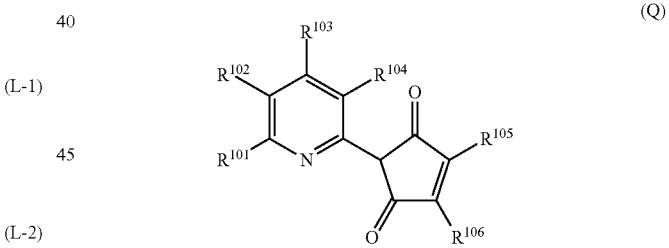
(Q)

(In Formula (Q), $R^{101}, R^{102}, R^{103}, R^{104}, R^{105}$, and $R^{106}$ mutually independently denote a hydrogen atom or a monovalent substituent. When at least two of $R^{101}, R^{102}, R^{103}, R^{104}, R^{105}$, and $R^{106}$ are at adjacent positions, they may be bonded to each other to form a 5- to 6-membered ring, and the ring may further have a substituent.)

<2> the curable coloring composition according to <1> above, wherein the curable coloring composition further comprises a polymerizable monomer, <3> a method for producing a color filter comprising a step of forming a pattern image by coating a support with the curable coloring composition according to <1> or <2> above, then imagewise exposing, and developing, <4> a color filter obtained by the production method according to <3> above, and <5> a quinophthalone dye represented by Formula (2).

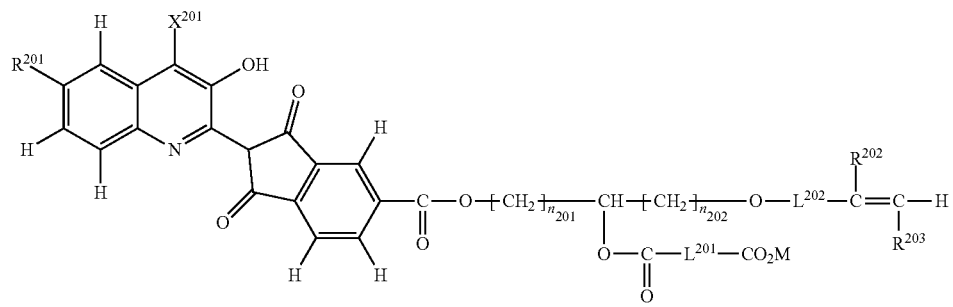

(In Formula (2), $X^{201}$ denotes a hydrogen atom or a halogen atom, $R^{201}$ denotes a hydrogen atom or a substituted or unsubstituted alkyl group, $R^{202}$ and $R^{203}$ mutually independently denote a hydrogen atom, a substituted or unsubstituted alkyl group, or a substituted or unsubstituted aryl group, M denotes a hydrogen atom, lithium, sodium, potassium, or an ammonium, $L^{201}$ denotes a divalent linking group selected from the group consisting of (L-1) to (L-4) below, $L^{202}$ denotes a divalent linking group selected from the group consisting of (L-4) to (L-7) below, $n_{201}$ denotes an integer of 0 to 2, and $n_{202}$ denotes an integer of 1 or 2.)

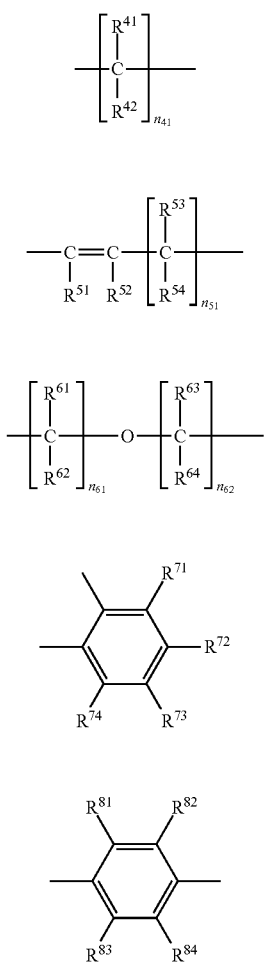

(In (L-1) to (L-7), $n_{41}$, $n_{51}$, $n_{61}$, and $n_{62}$ mutually independently denote an integer of 1 to 3, and $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ mutually independently denote a hydrogen atom or a monovalent substituent. When at least two of $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ are on the same carbon or at adjacent positions, they may be bonded to each other to form a 5- to 6-membered ring, and the ring may further have a substituent. In (L-1) to (L-4), a residue formed by removing $L^{201}$-$CO_2M$ from Formula (2) and a carboxyl group ($CO_2M$) may be bonded to either side, and in (L-4) to (L-7), a residue formed by removing $L^{202}$-$CR^{202}$=$CHR^{203}$ from Formula (2) and an ethylenically unsaturated group ($CR^{11}$=$CHR^{12}$) may be bonded to either side.)

MODE FOR CARRYING OUT THE INVENTION

Figure 1:
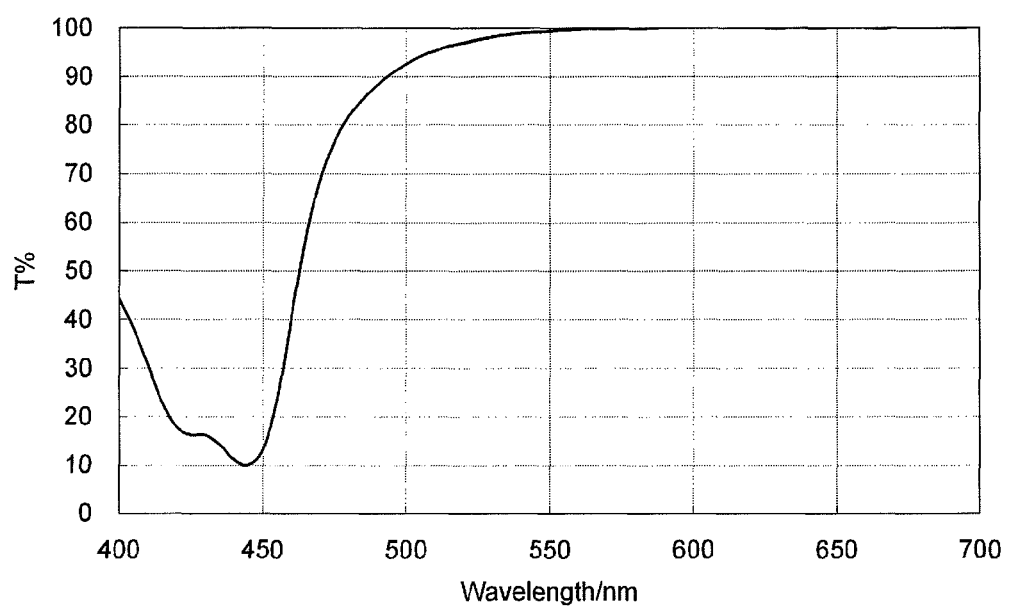
FIG. 1 is a transmission spectrum of a solution of quinophthalone dye (1) (example compound (1)) synthesized in Example 1.

The curable coloring composition, the color filter and the method for producing same, and the specific quinophthalone dye of the present invention are explained in detail below. Explanation of the constitutional requirements described below might be carried out based on a representative embodiment of the present invention, but the present invention should not be construed as being limited to such an embodiment. In the present specification, a numerical range expressed using 'to' means a range that includes the numeric values given before and after 'to' as a lower limit value and an upper limit value.

<Curable Coloring Composition>

The curable coloring composition of the present invention comprises at least one type of quinophthalone dye represented by Formula (1), which is described later.

The curable coloring composition of the present invention may be any as long as it is cured by light or heat, but preferably further comprises a radiation-sensitive compound or a polymerizable monomer. Furthermore, in general, it may be made up further using a solvent, and may be made up further using another component such as a binder or a crosslinking agent as necessary. The term resist solution has the same meaning as that of a curable composition.

<Quinophthalone Dye Represented by Formula (1)>

The quinophthalone dye used in the present invention is explained in detail.

Quinophthalone dyes are used in various applications as yellow dyes; for example, they are disclosed for use in sublimation transfer applications in JP-A-63-189289, JP-A-5-229268, etc. and for use in an inkjet printing application in JP-A-2001-311016. They are also disclosed as curable compositions in Patent Documents 5 and 6 above, etc.

Examples of quinophthalone dyes having at least one ethylenically unsaturated group-containing substituent and at least one carboxyl group include example compounds 22 and 39 described in Patent Document 7.

On the other hand, the quinophthalone dye used in the present invention is a quinophthalone dye represented by Formula (1) below. The quinophthalone dye represented by Formula (1) is a dye having at least one ethylenically unsaturated group-containing substituent and at least one carboxyl group as specific substituents, and having a specific structure. No dye having the features of a dye represented by Formula (1) below has been known at all until now, and it could not be anticipated that it would exhibit particularly excellent performance in application to a curable coloring composition that has high solubility in an organic solvent, high light fastness, high heat fastness, and excellent stability over time and solvent resistance after curing, and to a color filter that has good color hue, high transmittance, excellent light fastness, heat fastness, and solvent resistance and is compatible with high resolution.

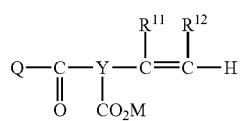

(1)

In Formula (1), $R^{11}$ and $R^{12}$ mutually independently denote a hydrogen atom, a substituted or unsubstituted alkyl group, or a substituted or unsubstituted aryl group.

The substituted or unsubstituted alkyl group denoted by $R^{11}$ or $R^{12}$ may be straight-chain, branched-chain, or cyclic, and the total number of carbons is preferably 1 to 15. Examples thereof include a methyl group, an ethyl group, an isopropyl group, an allyl group, and a cyclohexyl group.

The substituted or unsubstituted aryl group denoted by $R^{11}$ or $R^{12}$ may be monocyclic or fused ring, and the total number of carbons is preferably 6 to 15. Examples thereof include a phenyl group and a naphthyl group.

The substituent with which $R^{11}$ and $R^{12}$ may be substituted is not particularly limited, but representative examples thereof include a halogen atom, an aliphatic group (a saturated aliphatic group (meaning an alkyl group or a cyclic saturated aliphatic group including a cycloalkyl group, a bicycloalkyl group, a bridged cyclic saturated hydrocarbon group, and a spiro saturated hydrocarbon group), an unsaturated aliphatic group (meaning a chain-form unsaturated aliphatic group such as an alkenyl group or an alkenyl group or a cyclic unsaturated aliphatic group including a cycloalkenyl group, a bicycloalkenyl group, a bridged cyclic unsaturated hydrocarbon group, and a spiro unsaturated hydrocarbon group, having a double bond or triple bond)), an aryl group (preferably an optionally substituted phenyl group), a heterocyclic group (preferably a 5- to 8-membered ring comprising an oxygen atom, a sulfur atom, or a nitrogen atom as a ring member atom, and the ring may be fused with an alicyclic, aromatic, or heterocyclic ring), a cyano group, an aliphatic oxy group (represented by an alkoxy group), an aryloxy group, an acyloxy group, a carbamoyloxy group, an aliphatic oxycarbonyloxy group (represented by an alkoxycarbonyloxy group), an aryloxycarbonyloxy group, an amino group (including an aliphatic amino group (represented by an alkylamino group), an anilino group, and a heterocyclic amino group), an acylamino group, an aminocarbonylamino group, an aliphatic oxycarbonylamino group (represented by an alkoxycarbonylamino group), an aryloxycarbonylamino group, a sulfamoylamino group, an aliphatic (represented by alkyl) or aryl sulfonylamino group, an aliphatic thio group (represented by an alkylthio group), an arylthio group, a sulfamoyl group, an aliphatic (represented by alkyl) or aryl sulfinyl group, an aliphatic (represented by alkyl) or aryl sulfonyl group, an acyl group, an aryloxycarbonyl group, an aliphatic oxycarbonyl group (represented by an alkoxycarbonyl group), a carbamoyl group, an aryl or heterocyclic azo group, an imide group, an aliphatic oxysulfonyl group (represented by an alkoxysulfonyl group), an aryloxysulfonyl group, a hydroxy group, a nitro group, a carboxyl group, and a sulfo group, and each group may further have a substituent (e.g. the substituents cited here).

The substituent that may be used for substitution is explained below in further detail.

Examples of the halogen atom include a fluorine atom, a chlorine atom, a bromine atom, and an iodine atom. Among them, a chlorine atom and a bromine atom are preferable, and a chlorine atom is particularly preferable.

The aliphatic group is a straight-chain, branched, or cyclic aliphatic group, and as described above the saturated aliphatic group includes an alkyl group, a cycloalkyl group, and a bicycloalkyl group, which are optionally substituted. The number of carbon atoms thereof is preferably 1 to 30. Examples thereof include a methyl group, an ethyl group, an n-propyl group, an isopropyl group, a tert-butyl group, an n-octyl group, an eicosyl group, a 2-chloroethyl group, a 2-cyanoethyl group, a benzyl group, and a 2-ethylhexyl group. The cycloalkyl group referred to here includes a substituted or unsubstituted cycloalkyl group. The substituted or unsubstituted cycloalkyl group is preferably a cycloalkyl group having 3 to 30 carbons. Examples thereof include a cyclohexyl group, a cyclopentyl group, and a 4-n-dodecyl cyclohexyl group. As the bicycloalkyl group, there can be cited a substituted or unsubstituted bicycloalkyl group having 5 to 30 carbons, that is, a monovalent group formed by removing one hydrogen atom from a bicycloalkane having 5 to 30 carbons. Examples thereof include a bicyclo[2.2.1]heptan-2-yl group and a bicyclo[2.2.2]octan-3-yl group. A tricyclo structure, which has more ring structures, is also included.

The unsaturated aliphatic group is a straight-chain, branched, or cyclic unsaturated aliphatic group, and includes an alkenyl group, a cycloalkenyl group, a bicycloalkenyl group, and an alkynyl group. The alkenyl group includes a straight-chain, branched, or cyclic substituted or unsubstituted alkenyl group. The alkenyl group is preferably a substituted or unsubstituted alkenyl group having 2 to 30 carbons. Examples thereof include a vinyl group, an allyl group, a prenyl group, a geranyl group, and an oleyl group. The cycloalkenyl group is preferably a substituted or unsubstituted cycloalkenyl group having 3 to 30 carbons, that is, a monovalent group formed by removing one hydrogen atom from a cycloalkene having 3 to 30 carbons. Examples thereof include a 2-cyclopenten-1-yl group and a 2-cyclohexen-1-yl group. The bicycloalkenyl group includes a substituted or unsubstituted bicycloalkenyl group. The bicycloalkenyl group is preferably a substituted or unsubstituted bicycloalkenyl group having 5 to 30 carbons, that is, a monovalent group formed by removing one hydrogen atom from a bicycloalkene having one double bond. Examples thereof include a bicyclo[2.2.1]hept-2-en-1-yl group and a bicyclo[2.2.2]oct-2-en-4-yl group. The alkynyl group is preferably a substituted or unsubstituted alkynyl group having 2 to 30 carbons, and examples thereof include an ethynyl group and a propargyl group.

The aryl group is preferably a substituted or unsubstituted aryl group having 6 to 30 carbons; examples thereof include a phenyl group, a p-tolyl group, a naphthyl group, an m-chlorophenyl group, and an o-hexadecanoylaminophenyl group, and an optionally substituted phenyl group is preferable.

The heterocyclic group is a monovalent group formed by removing one hydrogen atom from a substituted or unsubstituted aromatic or non-aromatic heterocyclic compound, which may further be fused. These heterocyclic groups are preferably 5- or 6-membered heterocyclic groups, and the heteroatom as a ring member is preferably an oxygen atom, a sulfur atom, or a nitrogen atom. A 5- or 6-membered aromatic heterocyclic group having 3 to 30 carbons is more preferable. Examples of the heterocycle of the heterocyclic group include a pyridine ring, a pyrazine ring, a pyridazine ring, a pyrimidine ring, a triazine ring, a quinoline ring, an isoquinoline ring, a quinazoline ring, a cinnoline ring, a phthalazine ring, a quinoxaline ring, a pyrrole ring, an indole ring, a furan ring, a benzofuran ring, a thiophene ring, a benzothiophene ring, a pyrazole ring, an imidazole ring, a benzimidazole ring, a triazole ring, an oxazole ring, a benzoxazole ring, a thiazole ring, a benzothiazole ring, an isothiazole ring, a benzisothiazole ring, a thiadiazole ring, an isoxazole ring, a benzisoxazole ring, a pyrrolidine ring, a piperidine ring, a piperazine ring, an imidazolidine ring, and a thiazoline ring.

The aliphatic oxy group (represented by an alkoxy group) includes a substituted or unsubstituted aliphatic oxy group (represented by an alkoxy group), and the number of carbons is preferably 1 to 30. Examples thereof include a methoxy group, an ethoxy group, an isopropoxy group, an n-octyloxy group, a methoxyethoxy group, a hydroxyethoxy group, and a 3-carboxypropoxy group.

The aryloxy group is preferably a substituted or unsubstituted aryloxy group having 6 to 30 carbons. Examples of the aryloxy group include a phenoxy group, a 2-methylphenoxy group, a 4-tert-butylphenoxy group, a 3-nitrophenoxy group, and a 2-tetradecanoylaminophenoxy group. An optionally substituted phenyloxy group is preferable.

The acyloxy group is preferably a formyloxy group, a substituted or unsubstituted alkylcarbonyloxy group having 2 to 30 carbons, or a substituted or unsubstituted arylcarbonyloxy group having 6 to 30 carbons. Examples of the acyloxy group include a formyloxy group, an acetyloxy group, a pivaloyloxy group, a stearoyloxy group, a benzoyloxy group, and a p-methoxyphenylcarbonyloxy group.

The carbamoyloxy group is preferably a substituted or unsubstituted carbamoyloxy group having 1 to 30 carbons. Examples of the carbamoyloxy group include an N,N-dimethylcarbamoyloxy group, an N,N-diethylcarbamoyloxy group, a morpholinocarbonyloxy group, an N,N-di-n-octylaminocarbonyloxy group, and an N-n-octylcarbamoyloxy group.

The aliphatic oxycarbonyloxy group (represented by an alkoxycarbonyloxy group) preferably has 2 to 30 carbons and may have a substituent. Examples thereof include a methoxycarbonyloxy group, an ethoxycarbonyloxy group, a tert-butoxycarbonyloxy group, and an n-octylcarbonyloxy group.

The aryloxycarbonyloxy group is preferably a substituted or unsubstituted aryloxycarbonyloxy group having 7 to 30 carbons. Examples of the aryloxycarbonyloxy group include a phenoxycarbonyloxy group, a p-methoxyphenoxycarbonyloxy group, and a p-n-hexadecyloxyphenoxycarbonyloxy group. An optionally substituted phenoxycarbonyloxy group is preferable.

The amino group includes an amino group, an aliphatic amino group (represented by an alkylamino group), an arylamino group, and a heterocyclic amino group. The amino group is preferably a substituted or unsubstituted aliphatic amino group having 1 to 30 carbons (represented by an alkylamino group) or a substituted or unsubstituted arylamino group having 6 to 30 carbons. Examples of the amino group include an amino group, a methylamino group, a dimethylamino group, an anilino group, an N-methylanilino group, a diphenylamino group, a hydroxyethylamino group, a carboxyethylamino group, a sulfoethylamino group, a 3,5-dicarboxyanilino group, and a 4-quinolylamino group.

The acylamino group is preferably a formylamino group, a substituted or unsubstituted alkylcarbonylamino group having 1 to 30 carbons, or a substituted or unsubstituted arylcarbonylamino group having 6 to 30 carbons. Examples of the acylamino group include a formylamino group, an acetylamino group, a pivaloylamino group, a lauroylamino group, a benzoylamino group, and a 3,4,5-tri-n-octyloxyphenylcarbonylamino group.

The aminocarbonylamino group is preferably a substituted or unsubstituted aminocarbonylamino group having 1 to 30 carbons. Examples of the aminocarbonylamino group include a carbamoylamino group, an N,N-dimethylaminocarbonylamino group, an N,N-diethylaminocarbonylamino group, and a morpholinocarbonylamino group. The term 'amino' in this group has the same meaning as the 'amino' in the above-mentioned amino group.

The aliphatic oxycarbonylamino group (represented by an alkoxycarbonylamino group) preferably has 2 to 30 carbons and is optionally substituted. Examples thereof include a methoxycarbonylamino group, an ethoxycarbonylamino group, a tert-butoxycarbonylamino group, an n-octadecyloxycarbonylamino group, and an N-methylmethoxycarbonylamino group.

The aryloxycarbonylamino group is preferably a substituted or unsubstituted aryloxycarbonylamino group having 7 to 30 carbons. Examples of the aryloxycarbonylamino group include a phenoxycarbonylamino group, a p-chlorophenoxycarbonylamino group, and a m-n-octyloxyphenoxycarbonylamino group. An optionally substituted phenyloxycarbonylamino group is preferable.

The sulfamoylamino group is preferably a substituted or unsubstituted sulfamoylamino group having 0 to 30 carbons. Examples of the sulfamoylamino group include a sulfamoylamino group, an N,N-dimethylaminosulfonylamino group, and an N-n-octylaminosulfonylamino group.

The aliphatic (represented by alkyl) or aryl sulfonylamino group is preferably a substituted or unsubstituted aliphatic sulfonylamino group having 1 to 30 carbons (represented by an alkylsulfonylamino group), or a substituted or unsubstituted aryl sulfonylamino group having 6 to 30 carbons (preferably an optionally substituted phenylsulfonylamino group). Examples thereof include a methylsulfonylamino group, a butylsulfonylamino group, a phenylsulfonylamino group, a 2,3,5-trichlorophenylsulfonylamino group, and a p-methylphenylsulfonylamino group.

The aliphatic thio group (represented by an alkylthio group) is preferably a substituted or unsubstituted alkylthio group having 1 to 30 carbons. Examples of the alkylthio group include a methylthio group, an ethylthio group, and an n-hexadecylthio group.

The arylthio group is preferably a substituted or unsubstituted arylthio group having 6 to 12 carbons. Examples of the arylthio group include a phenylthio group, a 1-naphthylthio group, and a 2-naphthylthio group.

The sulfamoyl group is preferably a substituted or unsubstituted sulfamoyl group having 0 to 30 carbons. Examples of the sulfamoyl group include an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, and an N—(N'-phenylcarbamoyl)sulfamoyl) group.

The aliphatic (represented by alkyl) or aryl sulfinyl group is preferably a substituted or unsubstituted aliphatic sulfinyl group having 1 to 30 carbons (represented by an alkylsulfinyl group) or a substituted or unsubstituted arylsulfinyl group having 6 to 30 carbons (preferably an optionally substituted phenylsulfinyl group). Examples thereof include a methylsulfinyl group, an ethylsulfinyl group, a phenylsulfinyl group, and a p-methylphenylsulfinyl group.

The aliphatic (represented by alkyl) or aryl sulfonyl group is preferably a substituted or unsubstituted aliphatic sulfonyl group having 1 to 30 carbons (represented by an alkylsulfonyl group) or a substituted or unsubstituted aryl sulfonyl group having 6 to 30 carbons (preferably an optionally substituted phenylsulfonyl group). Examples thereof include a methylsulfonyl group, an ethylsulfonyl group, a phenylsulfonyl group, and a p-toluenesulfonyl group.

The acyl group is preferably a formyl group, a substituted or unsubstituted aliphatic carbonyl group having 2 to 30 carbons (represented by an alkylcarbonyl group), a substituted or unsubstituted arylcarbonyl group having 7 to 30 carbons (preferably an optionally substituted phenylcarbonyl group), or a substituted or unsubstituted heterocyclic carbonyl group having 4 to 30 carbons in which bonding to the carbonyl group is via a carbon atom. Examples thereof include an acetyl group, a pivaloyl group, a 2-chloroacetyl group, a stearoyl group, a benzoyl group, a p-n-octyloxyphenylcarbonyl group, a 2-pyridylcarbonyl group, and a 2-furylcarbonyl group.

The aryloxycarbonyl group is preferably a substituted or unsubstituted aryloxycarbonyl group having 7 to 30 carbons. Examples of the aryloxycarbonyl group include a phenoxycarbonyl group, an o-chlorophenoxycarbonyl group, an m-nitrophenoxycarbonyl group, and a p-tert-butylphenoxycarbonyl group. An optionally substituted phenyloxycarbonyl group is preferable.

The aliphatic oxycarbonyl group (represented by an alkoxycarbonyl group) preferably has 2 to 30 carbons and is optionally substituted. Examples thereof include a methoxycarbonyl group, an ethoxycarbonyl group, a tert-butoxycarbonyl group, and an n-octadecyloxycarbonyl group.

The carbamoyl group is preferably a substituted or unsubstituted carbamoyl group having 1 to 30 carbons. Examples of the carbamoyl group include a carbamoyl group, an N-methylcarbamoyl group, an N,N-dimethylcarbamoyl group, an N,N-di-n-octylcarbamoyl group, and an N-(methylsulfonyl)carbamoyl group.

Examples of the aryl or heterocyclic azo group include a phenylazo group, a 4-methoxyphenylazo group, a 4-pivaloylaminophenylazo group, and a 2-hydroxy-4-propanoylphenylazo group.

Examples of the imide group include an N-succinimide group and an N-phthalimide group.

The aliphatic oxysulfonyl group (represented by an alkoxysulfonyl group) preferably has 1 to 30 carbons and is optionally substituted. Examples thereof include a methoxysulfonyl group, an ethoxysulfonyl group, and an n-butoxysulfonyl group.

The aryloxysulfonyl group preferably has 6 to 12 carbons and is optionally substituted. Examples thereof include a phenoxysulfonyl group and a 2-naphthoxyphenyl group.

In addition to the above, examples include a hydroxy group, a cyano group, a nitro group, the above-mentioned dissociable group (e.g. a sulfo group, a carboxyl group, or a phosphono group), and an ethylenically unsaturated group-containing substituent.

Each of these groups may further have a substituent, and examples of such a substituent include the substituents described above.

In Formula (1), M denotes a hydrogen atom, lithium, sodium, potassium, a primary to tertiary amine, or a quaternary ammonium.

Examples of the ammonium denoted by M include unsubstituted ammonium ($NH_4^+$), primary to tertiary amine ammonium, and a quaternary ammonium; an ammonium having 1 to 15 carbons in total is preferable, and examples thereof include 2-ethylhexylammonium, diethylammonium, diisopropylammonium, dibutylammonium, triethylammonium, and diisopropylethylammonium. These substituents may further have a substituent, and examples of such a substituent include the substituents with which $R^{11}$ and $R^{12}$ above may be substituted.

Y denotes a trivalent linking group represented by (Y-1) or (Y-2).

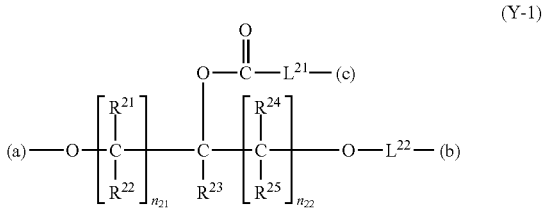

(Y-1)

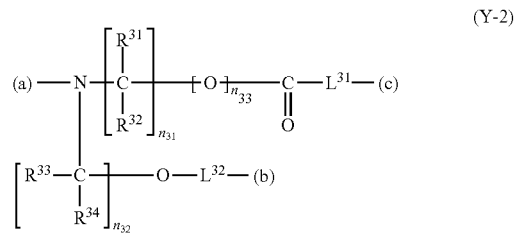

(Y-2)

In (Y-1) and (Y-2), $R^{21}$, $R^{22}$, $R^{23}$, $R^{24}$, $R^{25}$, $R^{31}$, $R^{32}$, $R^{33}$, and $R^{34}$ mutually independently denote a hydrogen atom, a substituted or unsubstituted alkyl group, a substituted or unsubstituted aryl group, or a substituted or unsubstituted heterocyclic group.

The substituted or unsubstituted alkyl group denoted by $R^{21}$, $R^{22}$, $R^{23}$, $R^{24}$, $R^{25}$, $R^{31}$, $R^{32}$, $R^{33}$, and $R^{34}$ may be straight-chain, branched chain, or cyclic, and an alkyl group having a total number of carbons of 1 to 15 is preferable. Examples thereof include a methyl group, an ethyl group, an isopropyl group, an allyl group, and a cyclohexyl group.

The substituted or unsubstituted aryl group denoted by $R^{21}$, $R^{22}$, $R^{23}$, $R^{24}$, $R^{25}$, $R^{31}$, $R^{32}$, $R^{33}$, and $R^{34}$ may be either monocyclic or fused, and an aryl group having a total number of carbons of 6 to 16 is preferable. Examples thereof include a phenyl group, a naphthyl group, a 2-chlorophenyl group, a 4-methylphenyl group, and a 4-methoxyphenyl group.

The substituted or unsubstituted heterocyclic group denoted by $R^{21}$, $R^{22}$, $R^{23}$, $R^{24}$, $R^{25}$, $R^{31}$, $R^{32}$, $R^{33}$, and $R^{34}$ is one in which its heterocyclic moiety has a heteroatom (e.g. a nitrogen atom, a sulfur atom, or an oxygen atom); it may be a saturated ring or an unsaturated ring, and it may be either monocyclic or fused. A heterocyclic group having a total number of carbons of 3 to 15 is preferable. Examples thereof include a 3-pyridyl group, a 2-pyrimidyl group, a 2-pyrazinyl group, and a 1-piperidinyl group.

$n_{21}$ and $n_{22}$ mutually independently denote an integer of 0 to 3.

$n_{31}$ and $n_{32}$ mutually independently denote an integer of 1 to 6.

$n_{33}$ denotes 0 or 1.

$L^{21}$ and $L^{31}$ denote a divalent linking group selected from the group consisting of (L-1) to (L-4), $L^{22}$ and $L^{32}$ denote a single bond or a divalent linking group selected from the group consisting of (L-4) to (L-7), (a) denotes a linking site to a carbonyl group bonded to a dye residue (Q), (b) denotes a linking site to an ethylenically unsaturated group ($CR^{11}=CHR^{12}$), and (c) denotes a linking site to a carboxyl group ($CO_2M$).

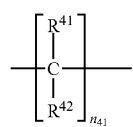
(L-1)

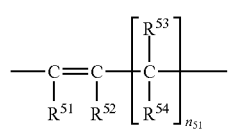
(L-2)

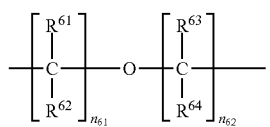
(L-3)

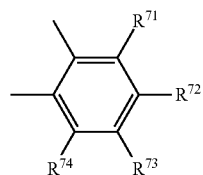
(L-4)

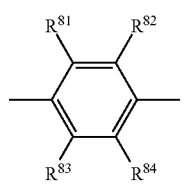
(L-5)

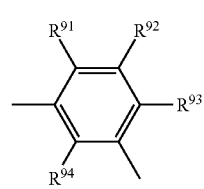
(L-6)

(L-7)

In (L-1) to (L-7), $n_{41}$, $n_{51}$, $n_{61}$, and $n_{62}$ mutually independently denote an integer of 1 to 3.

In (L-1) to (L-7), $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ mutually independently denote a hydrogen atom or a monovalent substituent. When at least two of $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ are on the same carbon or at adjacent positions, they may be bonded to each other to form a 5- to 6-membered ring, and the ring may further have a substituent.

The monovalent substituent denoted by $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ may be any as long as it is a substitutable group, and examples thereof include substituents cited for $R^{11}$ and $R^{12}$. These substituents may further have a substituent, and examples of such a substituent include the substituents with which $R^{11}$ and $R^{12}$ above may be substituted.

In (L-1) to (L-4), a residue formed by removing $L^{21}$ from (Y-1) or a residue formed by removing $L^{31}$ from (Y-2) and a carboxyl group ($CO_2M$) may be bonded to either side and, furthermore, in (L-4) to (L-7), a residue formed by removing $L^{22}$ from (Y-1) or a residue formed by removing $L^{32}$ from (Y-2) and an ethylenically unsaturated group ($CR^{11}=CHR^{12}$) may be bonded to either side.

Among them, Y is preferably a trivalent linking group represented by (Y-1), and a trivalent linking group represented by (Y-1') below is more preferable.

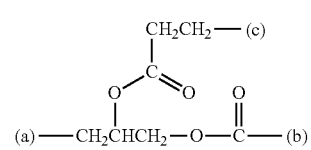
(Y-1')

Q denotes a dye residue formed by removing one hydrogen atom from any possible position of a dye represented by Formula (Q) below.

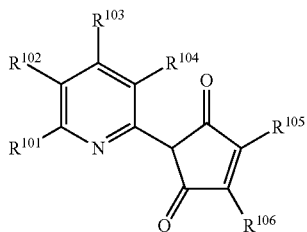

(Q)

In Formula (Q), $R^{101}$, $R^{102}$, $R^{103}$, $R^{104}$, $R^{105}$, and $R^{106}$ mutually independently denote a hydrogen atom or a monovalent substituent. The substituent denoted by $R^{101}$, $R^{102}$, $R^{103}$, $R^{104}$, $R^{105}$, and $R^{106}$ may be any as long as it is a substitutable group. Examples thereof include the substituents that can be used as a substituent on $R^{11}$ and $R^{12}$ described above, preferred examples include, mutually independently, a halogen atom, an aliphatic group, an aryl group, a heterocyclic group, a cyano group, an alkoxy group, an aryloxy group, an acyloxy group, a carbamoyloxy group, an aliphatic oxycarbonyloxy group, an aryloxycarbonyloxy group, an amino group, an anilino group, an acylamino group, an aminocarbonylamino group, an aliphatic oxycarbonylamino group, an aryloxycarbonylamino group, a sulfamoylamino group, an alkylthio group, an arylthio group, a sulfamoyl group, an alkyl or aryl sulfinyl group, an alkyl or aryl sulfonyl group, an acyl group, an aryloxycarbonyl group, an alkoxycarbonyl group, a carbamoyl group, an aryl or heterocyclic azo group, an imide group, a hydroxy group, a nitro group, a carboxyl group, and a sulfo group, and each group may further have a substituent (e.g. the substituents cited here).

When at least two of $R^{101}$, $R^{102}$, $R^{103}$, $R^{104}$, $R^{105}$, and $R^{106}$ are at adjacent positions, that is, when a plurality of groups from $R^{101}$, $R^{102}$, $R^{103}$, $R^{104}$, $R^{105}$, and $R^{106}$ are in a positional relationship in which they are bonded to for example adjacent carbon atoms, they may be bonded to each other to form a 5- to 6-membered ring, and the ring may further have a substituent. Examples of this 5- to 6-membered ring include a benzene ring, a naphthalene ring, a cyclohexane ring, and a furan ring, which may further have a substituent, and examples of this substituent includes the substituents that can be used as a substituent on $R^{11}$ or $R^{12}$ described above.

From the viewpoint of the effects of the present invention being exhibited effectively, $R^{11}$ is preferably a hydrogen atom or an unsubstituted alkyl group, more preferably a hydrogen atom or an unsubstituted alkyl group having 1 to 3 carbons, and most preferably a hydrogen atom or a methyl group.

From the viewpoint of the effects of the present invention being exhibited effectively, $R^{12}$ is preferably a hydrogen atom or an unsubstituted alkyl group, more preferably a hydrogen atom or an unsubstituted alkyl group having 1 to 3 carbons, and most preferably a hydrogen atom.

From the viewpoint of the effects of the present invention being exhibited effectively, $R^{21}$, $R^{22}$, $R^{23}$, $R^{24}$, $R^{33}$, $R^{34}$, $R^{41}$, $R^{42}$, $R^{53}$, $R^{54}$, $R^{61}$, $R^{62}$, $R^{63}$, and $R^{64}$ are, mutually independently, preferably a hydrogen atom or an unsubstituted alkyl group, more preferably a hydrogen atom or an unsubstituted alkyl group having 1 to 3 carbons, and most preferably a hydrogen atom.

From the viewpoint of the effects of the present invention being exhibited effectively, $R^{51}$ and $R^{52}$ are, mutually independently, preferably a hydrogen atom, a halogen atom, a carboxyl group, or an unsubstituted alkyl group, more preferably a hydrogen atom, a chlorine atom, a carboxyl group, or an unsubstituted alkyl group having 1 to 3 carbons, and most preferably a hydrogen atom, a chlorine atom, a carboxyl group, or a methyl group.

From the viewpoint of the effects of the present invention being exhibited effectively, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ are, mutually independently, preferably a hydrogen atom, a halogen atom, a carboxyl group, or an unsubstituted alkyl group, more preferably a hydrogen atom, a chlorine atom, a carboxyl group, or an unsubstituted alkyl group having 1 to 3 carbons, and most preferably a hydrogen atom, a chlorine atom, a carboxyl group, or a methyl group.

From the viewpoint of the effects of the present invention being exhibited effectively, $R^{101}$ and $R^{102}$ are, mutually independently, preferably a hydrogen atom, a halogen atom, an aliphatic group, an aliphatic oxy group, an aliphatic oxycarbonyl group, an aryloxycarbonyl group, or a carbamoyl group, and more preferably are bonded to each other to form, together with the carbon atoms to which $R^{101}$ and $R^{102}$ are bonded, a 6-membered ring.

From the viewpoint of the effects of the present invention being exhibited effectively, $R^{103}$ is preferably a hydrogen atom, a halogen atom, an aliphatic oxycarbonyl group, a carbamoyl group, an acylamino group, an aliphatic sulfonylamino group, or an arylsulfonylamino group, more preferably a hydrogen atom or a halogen atom, yet more preferably a hydrogen atom, a chlorine atom, or a bromine atom, particularly preferably a hydrogen atom or a bromine atom, and most preferably a hydrogen atom.

From the viewpoint of the effects of the present invention being exhibited effectively, $R^{104}$ is preferably a hydrogen atom, a hydroxy group, or an aliphatic oxy group, more preferably a hydrogen atom or a hydroxy group, and particularly preferably a hydroxy group.

From the viewpoint of the effects of the present invention being exhibited effectively, $R^{105}$ and $R^{106}$ are, mutually independently, preferably a hydrogen atom, a halogen atom, an aliphatic group, an aliphatic oxy group, an aliphatic oxycarbonyl group, an aryloxycarbonyl group, or a carbamoyl group, and more preferably are bonded to each other to form, together with the carbon atoms to which $R^{101}$ and $R^{102}$ are bonded, a 6-membered ring.

From the viewpoint of the effects of the present invention being exhibited effectively, M is preferably a hydrogen atom, lithium, or an ammonium, more preferably a hydrogen atom, a tertiary ammonium, or a quaternary ammonium, and most preferably a hydrogen atom.

From the viewpoint of the effects of the present invention being exhibited effectively, $n_{21}$ is preferably an integer of 0 to 3, more preferably an integer of 0 to 2, and most preferably 0 or 1.

From the viewpoint of the effects of the present invention being exhibited effectively, $n_{22}$ is preferably an integer of 0 to 3, more preferably an integer of 1 to 3, and most preferably 1 or 2.

From the viewpoint of the effects of the present invention being exhibited effectively, $n_{31}$ is preferably an integer of 1 to 6, more preferably an integer of 1 to 4, and most preferably 2 or 3.

From the viewpoint of the effects of the present invention being exhibited effectively, $n_{32}$ is preferably an integer of 1 to 6, more preferably an integer of 1 to 4, and most preferably 2 or 3.

From the viewpoint of the effects of the present invention being exhibited effectively, $n_{33}$ is preferably 0 or 1.

From the viewpoint of the effects of the present invention being exhibited effectively, Y is preferably (Y-1) or (Y-2), and more preferably (Y-1).

From the viewpoint of the effects of the present invention being exhibited effectively, $L^{21}$ and $L^{31}$ are, mutually independently, preferably (L-1), (L-3), or (L-4), more preferably (L-1) or (L-3), and most preferably (L-1).

From the viewpoint of the effects of the present invention being exhibited effectively, $L^{22}$ and $L^{32}$ are, mutually independently, preferably (L-4), (L-5), or (L-7), more preferably (L-5) or (L-7), and most preferably (L-7).

With regard to a preferred combination of substituents for the compound represented by Formula (1) above, a compound in which at least one of these substituents is the above-mentioned preferred group is preferable, a compound in which more of the various substituents are the above-mentioned preferred groups is more preferable, and a compound in which all of the substituents are the above-mentioned preferred groups is most preferable.

From the viewpoint of the effects of the present invention being exhibited effectively, the compound represented by Formula (1) is particularly preferably a compound represented by Formula (2).

<Quinophthalone Dye Represented by Formula (2)>

The quinophthalone dye represented by Formula (1) above is preferably a quinophthalone dye represented by Formula (2) below.

In the same way as for the quinophthalone dye represented by Formula (1), the quinophthalone dye represented by Formula (2) is a dye having at least one ethylenically unsaturated group-containing substituent and at least one carboxyl group as specific substituents, and having a specific structure. Of Formula (1), a quinophthalone dye represented by Formula (2) exhibits particularly excellent performance in applications of a curable coloring composition that has high solubility in an organic solvent in particular and high light fastness and heat fastness and has excellent stability over time and solvent resistance after curing and a color filter that has good color hue, high transmittance properties, excellent light fastness, heat fastness, and solvent resistance and is compatible with high resolution; since quinophthalone dyes represented by Formula (1), in particular, quinophthalone dyes represented by Formula (2), have not been known until now, such excellent performance thereof could not be anticipated.

In Formula (2), $X^{201}$ denotes a hydrogen atom or a halogen atom. Examples of the halogen atom denoted by $X^{201}$ include a chlorine atom and a bromine atom. Among them, $X^{201}$ is particularly preferably a hydrogen atom.

In Formula (2), $R^{201}$ denotes a hydrogen atom or a substituted or unsubstituted alkyl group. The substituted or unsubstituted alkyl group denoted by $R^{201}$ may be any of straight chain, branched chain, and cyclic chain, and the total number of carbons is preferably 1 to 6. Examples thereof include a methyl group, an ethyl group, an isopropyl group, a t-butyl group, and a cyclohexyl group. These substituents may further have a substituent, and examples of such a substituent include the substituents with which $R^{11}$ and $R^{12}$ above may be substituted. Among them, $R^{201}$ is preferably a hydrogen atom or an alkyl group having 1 to 3 carbons, more preferably a hydrogen atom or an isopropyl group, and particularly preferably an isopropyl group.

In Formula (2), $R^{202}$ and $R^{203}$ mutually independently denote a hydrogen atom, a substituted or unsubstituted alkyl group, or a substituted or unsubstituted aryl group.

The substituted or unsubstituted alkyl group denoted by $R^{202}$ or 8203 may be straight-chain, branched chain, or cyclic, and the total number of carbons is preferably 1 to 15. Examples thereof include a methyl group, an ethyl group, an isopropyl group, an allyl group, and a cyclohexyl group.

The substituted or unsubstituted aryl group denoted by $R^{202}$ or $R^{203}$ may be either monocyclic or fused, and the total number of carbons is preferably 6 to 15. Examples thereof include a phenyl group and a naphthyl group.

M in Formula (2) has the same meaning as M of Formula (1), and preferred examples are also the same.

$n_{201}$ denotes an integer of 0 to 2, and $n_{202}$ denotes 1 or 2.

$L^{201}$ denotes a divalent linking group selected from the group consisting of (L-1) to (L-4), and $L^{202}$ denotes a divalent linking group selected from the group consisting of (L-4) to (L-7).

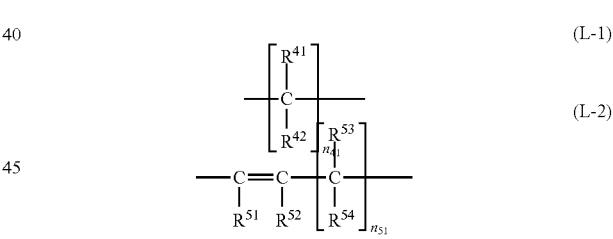

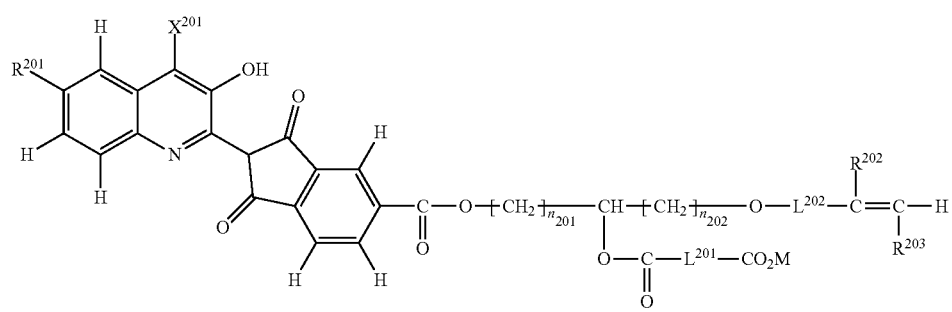

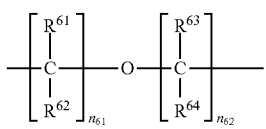 (L-3)

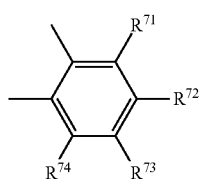 (L-4)

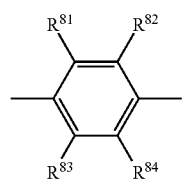 (L-5)

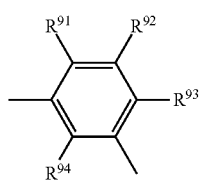 (L-6)

 (L-7)

(L-1) to (L-7) have the same meanings as those of the above-mentioned (L-1) to (L-7), and preferred examples are also the same.

From the viewpoint of the effects of the present invention being exhibited effectively, $X^{201}$ is preferably a hydrogen atom, a chlorine atom, or a bromine atom, more preferably a hydrogen atom or a bromine atom, and most preferably a hydrogen atom.

From the viewpoint of the effects of the present invention being exhibited effectively, $R^{201}$ is preferably a hydrogen atom or an unsubstituted alkyl group having 1 to 6 carbons, more preferably a hydrogen atom or an unsubstituted alkyl group having 1 to 5 carbons, and most preferably a hydrogen atom or an unsubstituted alkyl group having 1 to 4 carbons.

From the viewpoint of the effects of the present invention being exhibited effectively, $R^{202}$ is preferably a hydrogen atom or an unsubstituted alkyl group, more preferably a hydrogen atom or an unsubstituted alkyl group having 1 to 3 carbons, and most preferably a hydrogen atom or a methyl group.

From the viewpoint of the effects of the present invention being exhibited effectively, $R^{203}$ is preferably a hydrogen atom or an unsubstituted alkyl group, more preferably a hydrogen atom or an unsubstituted alkyl group having 1 to 3 carbons, and most preferably a hydrogen atom.

From the viewpoint of the effects of the present invention being exhibited effectively, $L^{201}$ is, mutually independently, preferably (L-1), (L-3), or (L-4), more preferably (L-1) or (L-3), and most preferably (L-1).

From the viewpoint of the effects of the present invention being exhibited effectively, $L^{202}$ is, mutually independently, preferably (L-4), (L-5), or (L-7), more preferably (L-5) or (L-7), and most preferably (L-7).

With regard to a preferred combination of substituents for the compound represented by Formula (2) above, a compound in which at least one of these substituents is the above-mentioned preferred group is preferable, a compound in which more of the various substituents are the above-mentioned preferred groups is more preferable, and a compound in which all of the substituents are the above-mentioned preferred groups is most preferable.

From the viewpoint of the effects of the present invention being exhibited effectively, the combination is preferably such that $X^{201}$ is a hydrogen atom or a bromine atom, $R^{201}$ is a hydrogen atom or an alkyl group having 1 to 4 carbons, $R^{202}$ is a hydrogen atom or a methyl group, $R^{203}$ is a hydrogen atom, $L^{201}$ is (L-1) (in the case of (L-1), $R^{41}$ and $R^{42}$ are hydrogen atoms, and $n_{41}$ is 2 or 3), (L-3) (in the case of (L-3), $R^{61}$, $R^{62}$, $R^{63}$, and $R^{64}$ are mutually independently a hydrogen atom or a methyl group, and $n_{61}$ and $n_{62}$ are 1 or 2), or (L-4) (in the case of (L-4), $R^{71}$, $R^{73}$, and $R^{74}$ are hydrogen atoms, and $R^{72}$ is a hydrogen atom, a methyl group, or a carboxyl group), $L^{202}$ is (L-5) (in the case of (L-5), $R^{81}$, $R^{82}$, $R^{83}$, and $R^{84}$ are hydrogen atoms) or (L-7), $n^{201}$ is 0 or 1, $n^{202}$ is 1 or 2, and M is a hydrogen atom, a trialkylammonium, or a tetraalkylammonium.

From the viewpoint of the effects of the present invention being exhibited effectively, the combination is more preferably such that $X^{201}$ is a hydrogen atom or a bromine atom, $R^{201}$ is a hydrogen atom or an alkyl group having 1 to 4 carbons, $R^{202}$ is a hydrogen atom or a methyl group, $R^{203}$ is a hydrogen atom, $L^{201}$ is (L-1) (in the case of (L-1), $R^{41}$ and $R^{42}$ are hydrogen atoms, and $n_{41}$ is 2 or 3), (L-3) (in the case of (L-3), $R^{61}$, $R^{62}$, $R^{63}$, and $R^{64}$ are mutually independently a hydrogen atom or a methyl group, and $n_{61}$ and $n_{62}$ are 1 or 2), or (L-4) (in the case of (L-4), $R^{71}$, $R^{73}$, and $R^{74}$ are hydrogen atoms and $R^{72}$ is a hydrogen atom or a carboxyl group), $L^{202}$ is (L-7), $n^{201}$ is 0 or 1, $n^{202}$ is 1 or 2, and M is a hydrogen atom, a trialkylammonium, or a tetraalkylammonium.

From the viewpoint of the effects of the present invention being exhibited effectively, the combination is most preferably such that $X^{201}$ is a hydrogen atom, $R^{201}$ is a branched alkyl group having 3 to 4 carbons, $R^{202}$ is a hydrogen atom or a methyl group, $R^{203}$ is a hydrogen atom, $L^{201}$ is (L-1) (in the case of (L-1), $R^{41}$ and $R^{42}$ are hydrogen atoms and $n_{41}$ is 2 or 3), (L-3) (in the case of (L-3), $R^{61}$, $R^{62}$, $R^{63}$, and $R^{64}$ are mutually independently a hydrogen atom or a methyl group, and $n_{61}$ and $n_{62}$ are 1 or 2), (L-4) (in the case of (L-4), $R^{71}$, $R^{73}$, and $R^{74}$ are hydrogen atoms and $R^{72}$ is a hydrogen atom or a carboxyl group), $L^{202}$ is (L-7), $n^{201}$ group), n is 0 or 1, $n^{202}$ is 1 or 2, and M is a hydrogen atom, a trialkylammonium having a total of 6 to 12 carbons, or tetramethylammonium.

Among them, the compound represented by Formula (2) above is preferably a compound represented by Formula (2') below.

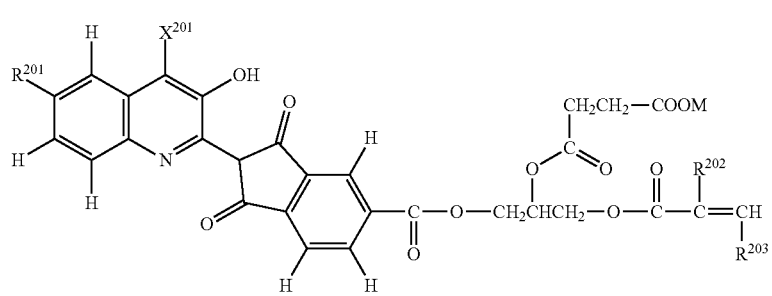

(In Formula (2'), $X^{201}$ denotes a hydrogen atom or a halogen atom, $R^{201}$ denotes a hydrogen atom or a substituted or unsubstituted alkyl group, and M denotes a hydrogen atom, lithium, sodium, potassium, or an ammonium.)

Specific examples of the compound represented by Formula (1) above are shown below, but the present invention should not be construed as being limited thereto. Furthermore, example compounds (1) to (56) below are example compounds of Formula (2) above. In addition, $R^1$, $R^2$, and X in Table 1 to Table 7 below are groups shown in Formula (3) below.

TABLE 1

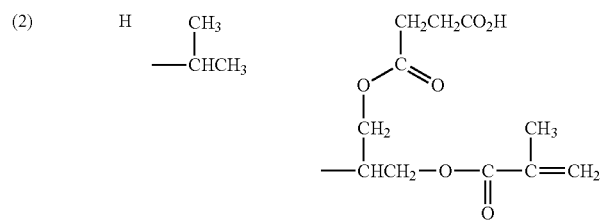

| Example Compounds | X | $R^1$ | $R^2$ |
|---|---|---|---|
| (1) | H | —CH(CH₃)CH₃ | —CH₂CH(OC(O)CH₂CH₂CO₂H)CH₂—O—C(O)—C(CH₃)=CH₂ |
| (2) | H | —CH(CH₃)CH₃ | —CH(CH₂OC(O)CH₂CH₂CO₂H)CH₂—O—C(O)—C(CH₃)=CH₂ |

TABLE 1-continued

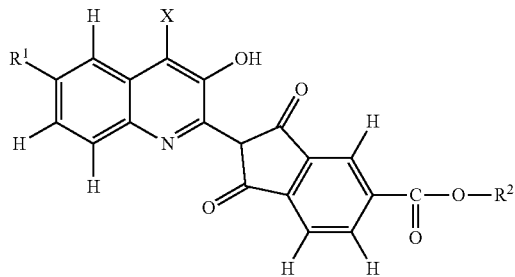
(3)

| Example Compounds | X | R[1] | R[2] |
|---|---|---|---|
| (3) | H | —CHCH₃(CH₃) | CH₂CH₂CH₂-CH(CO₂H)-C(=O)-O-CH₂CH₂-O-C(=O)-C(CH₃)=CH₂ |
| (4) | H | —CHCH₃(CH₃) | CH₂-CH(CH₂CH₂CO₂H)-C(=O)-O-CH₂-CH(-)CH₂-O-C(=O)-C(CH₃)=CH₂ |
| (5) | H | —CHCH₃(CH₃) | CH₂CH₂-CH(CO₂H)-C(=O)-O-CH₂CHCH₂-O-C(=O)-CH=CH₂ |
| (6) | H | —CHCH₃(CH₃) | CH₂-CH(CH₂CH₂CO₂H)-C(=O)-O-CH₂-CHCH₂-O-C(=O)-CH=CH₂ |
| (7) | H | —CHCH₃(CH₃) | CH₂CH₂-CH(CO₂H)-C(=O)-O-CH₂CH₂-O-C₆H₄-CH=CH₂ |
| (8) | H | —CHCH₃(CH₃) | CH₂-CH(CH₂CH₂CO₂H)-C(=O)-O-CH₂-CHCH₂-O-C₆H₄-CH=CH₂ |

TABLE 1-continued

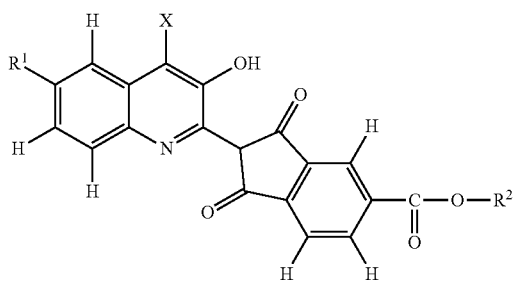

(3)

| Example Compounds | X | R¹ | R² |
|---|---|---|---|
| (9) | H | —CHCH₃ with CH₃ | —CH₂CHCH₂—O—C(=O)—CH=CH₂ with branch CH₂—O—C(=O)—CH₂—O—CH₂CO₂H |

TABLE 2

| Example Compounds | X | R¹ | R² |
|---|---|---|---|
| (10) | H | —CHCH₃ with CH₃ | —CHCH₂—O—C(=O)—CH=CH₂ with branch O—C(=O)—CH₂—CH₂—O—CH₂CO₂H |
| (11) | H | —CHCH₃ with CH₃ | —CH₂CHCH₂—O—C(=O)—CH=CH₂ with branch O—C(=O)—CH₂—C(CO₂H)=CH₂ |
| (12) | H | —CHCH₃ with CH₃ | —CHCH₂—O—C(=O)—CH=CH₂ with branch O—C(=O)—CH₂—C(CO₂H)=CH₂ |

TABLE 2-continued

| Example Compounds | X | R¹ | R² |
|---|---|---|---|
| (13) | H | —CHCH₃ with CH₃ | 2-(CO₂H)phenyl—C(=O)—O—CH₂CH₂—O—C(=O)—CH=CH₂ |
| (14) | H | —CHCH₃ with CH₃ | 2-(CO₂H)phenyl—C(=O)—O—CH₂—CHCH₂—O—C(=O)—CH=CH₂ |
| (15) | H | —CHCH₃ with CH₃ | 2,4-(CO₂H)₂phenyl—C(=O)—O—CH₂CH₂—O—C(=O)—CH=CH₂ |

TABLE 2-continued
| Example Compounds | X | R¹ | R² |
|---|---|---|---|
| (16) | H | —CHCH₃ (CH₃) |  |
| (17) | H | —CHCH₃ (CH₃) | 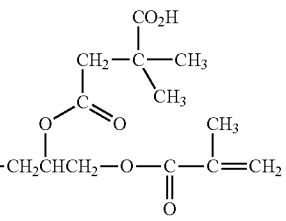 |
TABLE 3
| Example Compounds | X | R¹ | R² |
|---|---|---|---|
| (18) | H | —CHCH₃ (CH₃) |  |
| (19) | H | —CHCH₃ (CH₃) | 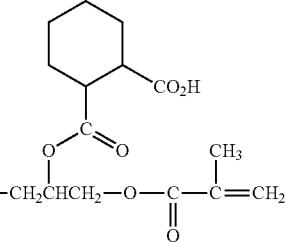 |
| (20) | H | —CHCH₃ (CH₃) |  |
| (21) | H | —CHCH₃ (CH₃) | 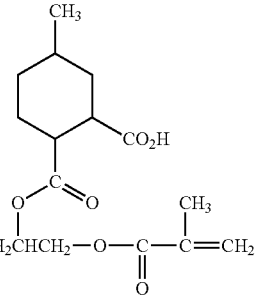 |

TABLE 3-continued

| Example Compounds | X | R¹ | R² |
|---|---|---|---|
| (22) | H | —CHCH₃ with CH₃ branch | structure with CH₂—C(CH₃)(CH₂CO₂H)—C(=O)—O—CH₂CHCH₂—O—C(=O)—C(CH₃)=CH₂ |
| (23) | H | —CHCH₃ with CH₃ branch | structure with CH₂CO₂H, CH=C(CH₂CO₂H)—C(=O)—O—CH₂CHCH₂—O—C(=O)—C(CH₃)=CH₂ |
| (24) | H | —CH₃ | structure with CH₂CO₂H, CH=C(CH₂CO₂H)—C(=O)—O—CH₂CHCH₂—O—C(=O)—C(CH₃)=CH₂ |
| (25) | H | —CH₃ | CH₂CH₂CO₂H—C(=O)—O—CH₂CHCH₂—O—(phenyl)—CH=CH₂ |

TABLE 4

| Example Compounds | X | R¹ | R² |
|---|---|---|---|
| (26) | H | —CH₂CH₃ | CH₂CH₂CO₂H—C(=O)—O—CH₂CHCH₂—O—C(=O)—C(CH₃)=CH₂ |
| (27) | H | —CH₂CH₂CH₃ | CH₂CH₂CO₂H—C(=O)—O—CHCH₂CH₂—O—C(=O)—C(CH₃)=CH₂ |
| (28) | H | —CH₂CH₂CH₂CH₃ | CH₂CH₂CH₂CO₂H—C(=O)—O—CH₂CHCH₂—O—C(=O)—C(CH₃)=CH₂ |

TABLE 4-continued
| Example Compounds | X | R$^1$ | R$^2$ |
|---|---|---|---|
| (29) | H | H | 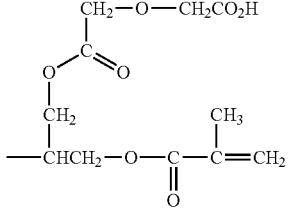 |
| (30) | H | H | 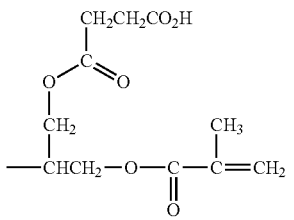 |
| (31) | H | H | 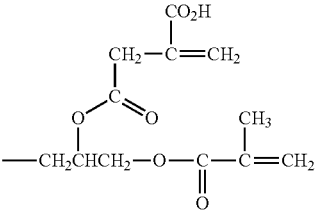 |
| (32) | H | H | 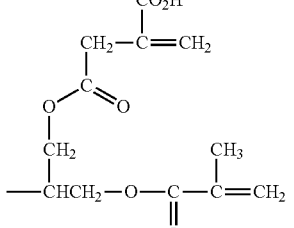 |
| (33) | H | H | 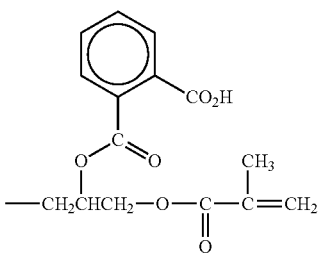 |

TABLE 5
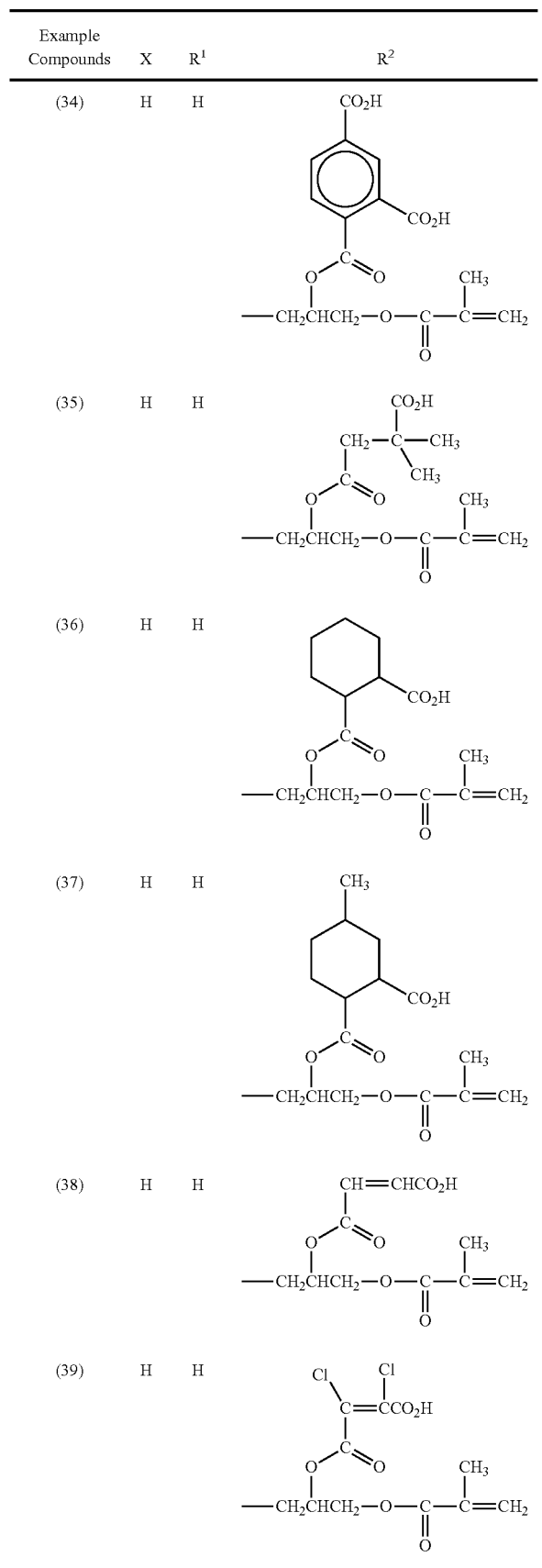
TABLE 5-continued
TABLE 6
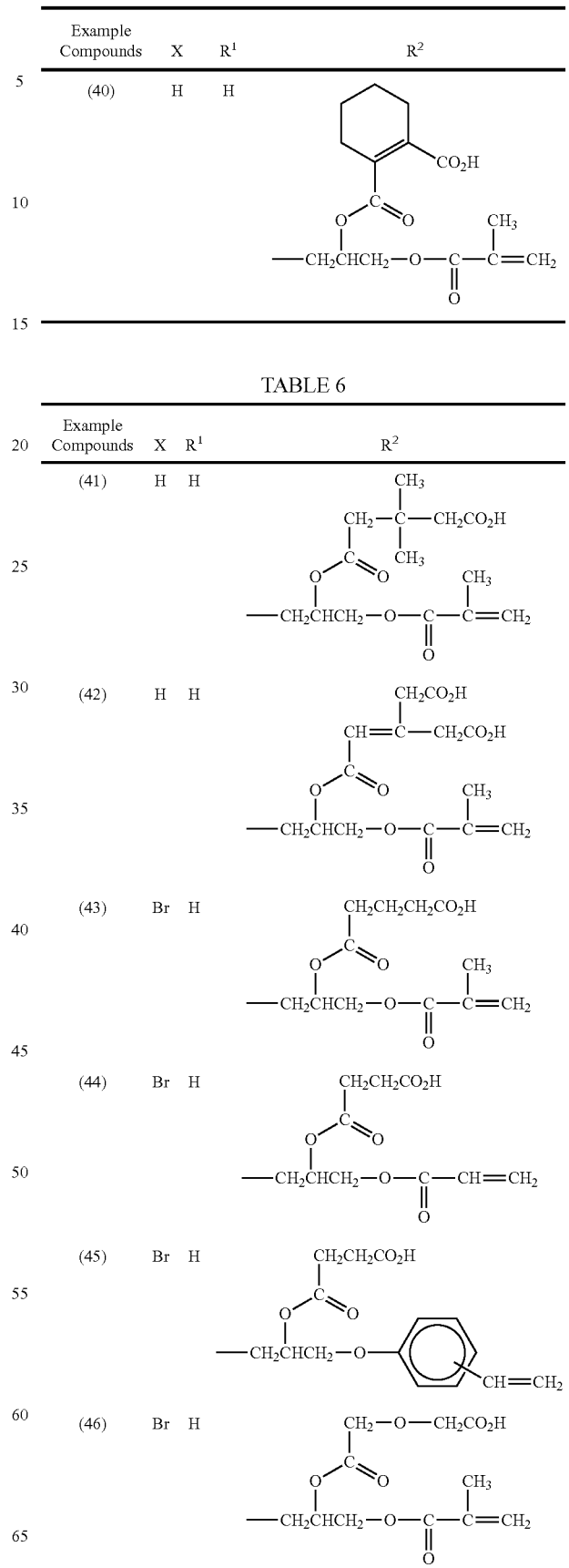

TABLE 6-continued

| Example Compounds | X | R¹ | R² |
|---|---|---|---|
| (47) | Br | H | (structure: 1,2,4-benzenetricarboxylic acid derivative with –CH₂CHCH₂–O–C(=O)–C(CH₃)=CH₂ ester linkage) |
| (48) | Br | H | (structure: HO₂C–C(CH₃)₂–CH₂–C(=O)–O–CH₂CHCH₂–O–C(=O)–C(CH₃)=CH₂) |

TABLE 7

| Example Compounds | X | R¹ | R² |
|---|---|---|---|
| (49) | Br | H | (structure: cyclohexane-1,2-dicarboxylic acid mono-ester with –CH₂CHCH₂–O–C(=O)–C(CH₃)=CH₂) |
| (50) | Br | H | (structure: 4-methylcyclohexane-1,2-dicarboxylic acid mono-ester with –CH₂CHCH₂–O–C(=O)–C(CH₃)=CH₂) |
| (51) | Br | H | (structure: CH=CHCO₂H maleic/fumaric mono-ester with –CH₂CHCH₂–O–C(=O)–C(CH₃)=CH₂) |

TABLE 7-continued

| Example Compounds | X | R¹ | R² |
|---|---|---|---|
| (52) | Br | H | (structure: Cl₂C=C(CO₂H)–C(=O)–O–CH₂CH₂–O–C(=O)–C(CH₃)=CH₂) |
| (53) | Br | H | (structure: cyclohexene-1,2-dicarboxylic acid mono-ester with –CH₂CHCH₂–O–C(=O)–C(CH₃)=CH₂) |
| (54) | Br | H | (structure: HO₂CCH₂–C(CH₃)₂–CH₂–C(=O)–O–CH₂CHCH₂–O–C(=O)–C(CH₃)=CH₂) |
| (55) | Br | H | (structure: (HO₂CCH₂)(CH=)C–CH₂CO₂H fragment with –C(=O)–O–CH₂CHCH₂–O–C(=O)–C(CH₃)=CH₂) |
| (56) | Cl | H | (structure: HO₂CCH₂CH₂–C(=O)–O–CH₂CHCH₂–O–C(=O)–C(CH₃)=CH₂) |

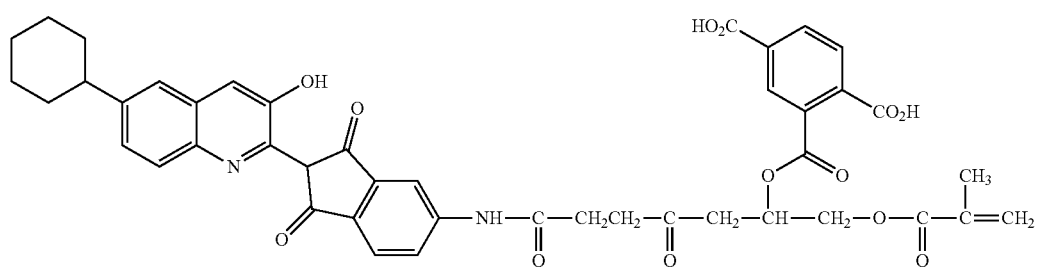
(57)
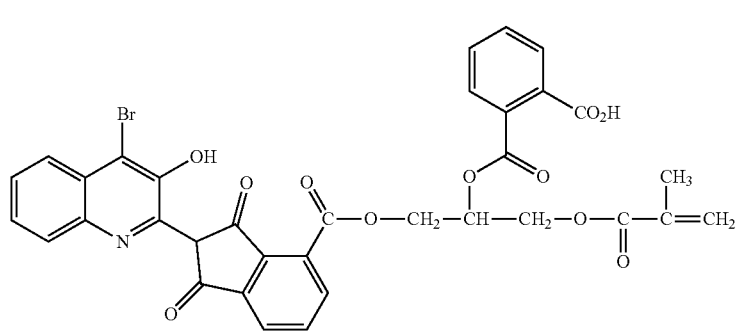
(58)
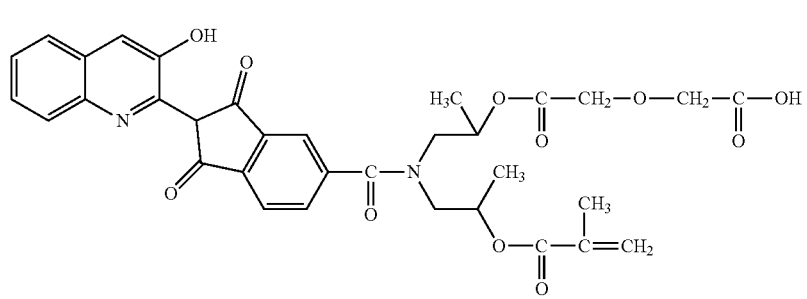
(59)
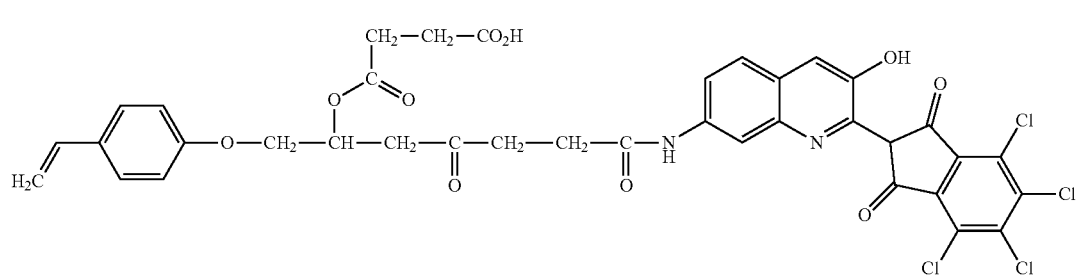
(60)
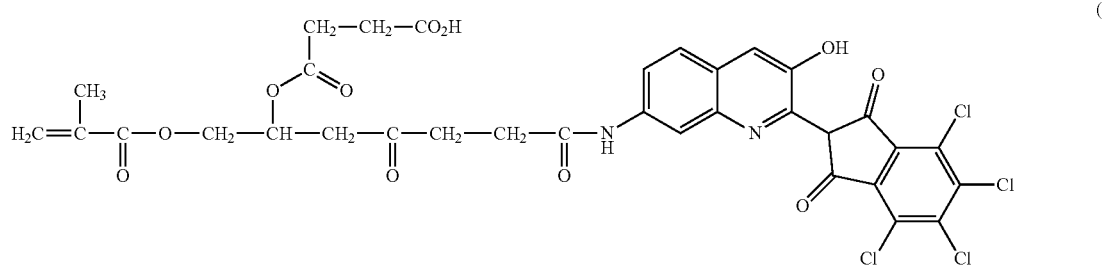
(61)

-continued

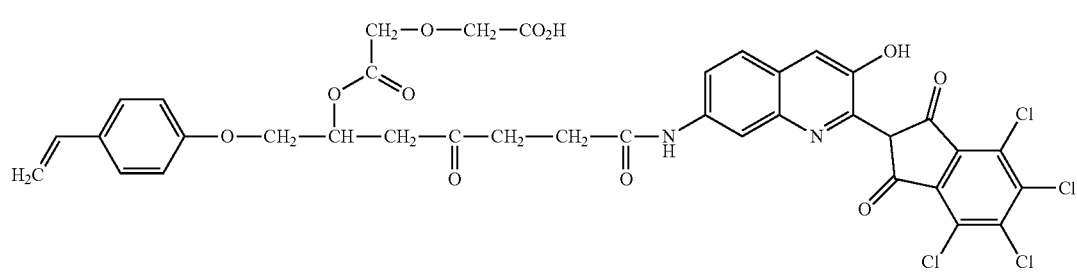

(62)

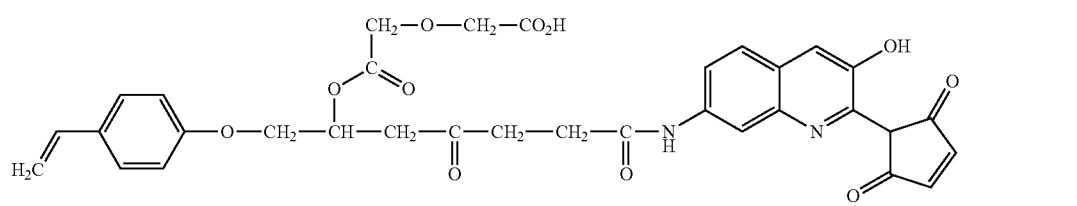

(63)

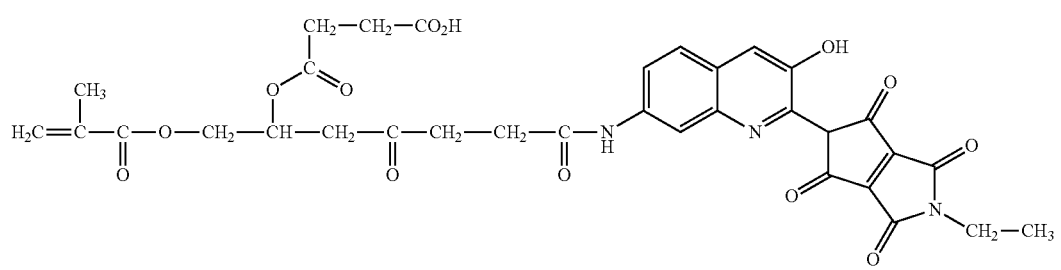

(64)

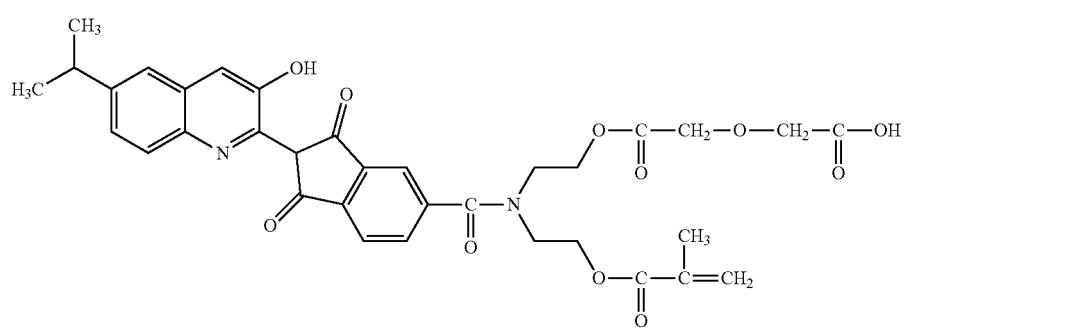

(65)

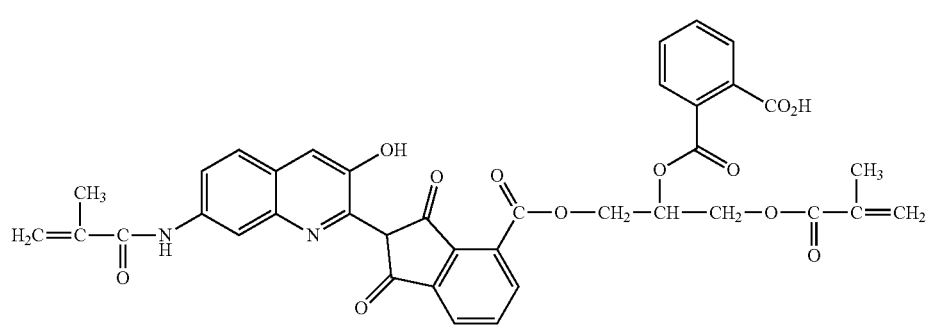

(66)

With regard to a method for synthesizing a quinophthalone dye represented by Formula (1) above in the present invention, it may be synthesized in accordance with a method for synthesizing a dye of Formula (1) described in JP-B-7-49583 or a dye of Formula (1) described in JP-B-5-5257. Specific explanation is given in Examples, which are described later.

The total concentration of the quinophthalone dye represented by Formula (1) above in the curable coloring composition depends on its molecular weight and molar extinction coefficient, but is preferably 0.5 to 80 weight % relative to the total solids content of the composition, more preferably 0.5 to 70 weight %, and particularly preferably 1 to 70 weight %.

Binder

The curable coloring composition of the present invention may comprise a binder as necessary.

The binder that can be used in the present invention is not particularly limited as long as it is alkali soluble, and is preferably selected from the viewpoint of heat fastness, developability, availability, etc.

The alkali-soluble binder is preferably a linear organic polymer, soluble in an organic solvent, and developable with a weakly alkaline aqueous solution. Examples of such a linear organic polymer include polymers having a carboxylic acid in a side chain, for example methacrylic acid copolymers, acrylic acid copolymers, itaconic acid copolymers, crotonic acid copolymers, maleic acid copolymers, and partially esterified maleic acid copolymers as described in the specifications of JP-A-59-44615, JP-B-54-34327, JP-B-58-12577, JP-B-54-25957, JP-A-59-53836, and JP-A-59-71048, and acidic cellulose derivatives similarly having a carboxylic acid in a side chain are useful. Other useful binders include polymers prepared by adding an acid anhydride to a polymer having a hydroxy group, polyhydroxystyrene resins, polysiloxane resins, poly(2-hydroxyethyl(meth)acrylate), polyvinylpyrrolidone, polyethylene oxide, and polyvinyl alcohol.

The binder resin may contain a monomer having a hydrophilic group as a copolymerization component. Examples of such a monomer include an alkoxyalkyl(meth)acrylate, a hydroxyalkyl(meth)acrylate, glycerol (meth)acrylate, (meth)acrylamide, N-methylolacrylamide, sec- and tert-alkylacrylamides, a dialkylaminoalkyl(meth)acrylate, morpholino (meth)acrylate, N-vinylpyrrolidone, N-vinylcaprolactam, vinylimidazole, vinyltriazole, methyl (meth)acrylate, ethyl (meth)acrylate, branched or linear propyl(meth)acrylate, branched or linear butyl(meth)acrylate, and phenoxyhydroxypropyl (meth)acrylate.

Other useful monomers having a hydrophilic group include monomers having a tetrahydrofurfuryl group, a phosphoric acid moiety, a phosphate ester moiety, a quaternary ammonium salt moiety, an ethyleneoxy chain, a propyleneoxy chain, a moiety of sulfonic acid or a salt thereof, a morpholinoethyl group, etc.

The binder may have a polymerizable group in a side chain for improving cross linking efficiency. A polymer containing an allyl group, a (meth)acrylic group, an allyloxyalkyl group, etc. in a side chain is also useful.

Examples of the polymer having such a polymerizable group include KS RESIST 106 (manufactured by Osaka Organic Chemical Industries, Ltd.) and the CYCLOMER-P Series (manufactured by Daicel Chemical Industries, Ltd.).

Alcohol-soluble nylons, polyethers of 2,2-bis(4-hydroxyphenyl)propane and epichlorohydrin, etc. are also useful for enhancing the strength of a cured coating film.

Among the above-mentioned binders, from the viewpoint of heat fastness, polyhydroxystyrene resins, polysiloxane resins, acrylic resins, acrylamide resins, and acrylic/acrylamide copolymer resins are preferable, and from the viewpoint of controlling developability, acrylic resins, acrylamide resins, and acrylic/acrylamide copolymer resins are preferable. Preferable acrylic resins include copolymers comprising monomers selected from benzyl (meth)acrylate, (meth)acrylic acid, hydroxyethyl(meth)acrylate, (meth)acrylamide, etc., KS-RESIST 106 (manufactured by Osaka Organic Chemical Industries, Ltd.), and the CYCLOMER-P Series (manufactured by Daicel Chemical Industries Co.).

An alkali-soluble phenol resin may be used as the binder that can be used in the present invention. When the curable coloring composition of the present invention is a positive-working composition, the alkali-soluble phenol resin can be favorably used therein. Examples of the alkali-soluble phenol resin include a novolac resin and a vinyl polymer.

The novolac resin can be obtained, for example, by condensation of a phenol and an aldehyde in the presence of an acid catalyst. Examples of the phenol include phenol, cresol, ethylphenol, butylphenol, xylenol, phenylphenol, catechol, resorcinol, pyrogallol, naphthol, and bisphenol A. The phenols may be used singly or in a combination of two or more types.

Examples of the aldehyde include formaldehyde, paraformaldehyde, acetaldehyde, propionaldehyde, and benzaldehyde.

Specific examples of the novolac resin include metacresol, and paracresol, and a condensation product of a mixture of metacresol and paracresol with formalin. The molecular weight distribution of the novolac resin may be adjusted by a method such as fractionation. Also, low molecular weight components having a phenolic hydroxy group such as bisphenol C and bisphenol A may be added to the novolac resin.

The weight-average molecular weight (as converted to a polystyrene-equivalent value measured by the GPC method) of the binder is preferably $1 \times 10^3$ to $2 \times 10^5$, more preferably $2 \times 10^3$ to $1 \times 10^5$, and particularly preferably $5 \times 10^3$ to $5 \times 10^4$.

The content of the binder in the curable coloring composition of the present invention is preferably 0 to 90 weight %, more preferably 0 to 70 weight %, and particularly preferably 0 to 60 weight %, relative to the total solids content in the composition.

Crosslinking Agent

The curable coloring composition of the present invention may comprise a crosslinking agent as necessary. When used together with the above-mentioned dye related to the present invention, a curing reaction of a film proceeds to a higher degree compared with the art, and a film having good curing properties is obtained, but it is also possible to obtain a film that has been cured to a yet higher degree by supplementarily using a crosslinking agent. It is useful from the viewpoint of achieving higher resolution of the curable coloring composition of the present invention.

The crosslinking agent that can be used in the present invention is not particularly limited as long as the film may be cured by a crosslinking reaction. Examples of the crosslinking agent include (a) an epoxy resin, (b) a melamine compound, guanamine compound, glycoluril compound, or urea compound substituted with at least one group selected from the group consisting of a methylol group, an alkoxymethyl group, and an acyloxymethyl group, and (c) a phenol compound, naphthol compound, or hydroxyanthracene compound substituted with at least one group selected from a methylol group, an alkoxymethyl group, and an acyloxymethyl group. Specifically, a polyfunctional epoxy resin is preferable.

As the epoxy resin (a), any crosslinkable compound having an epoxy group may be used; examples thereof include divalent glycidyl group-containing low molecular weight compounds such as bisphenol A diglycidyl ether, ethylene glycol diglycidyl ether, ethylene glycol diglycidyl ether, butanediol diglycidyl ether, hexanediol diglycidyl ether, dihydroxybiphenyl diglycidyl ether, diglycidyl phthalate, and N,N-diglycidylaniline; trivalent glycidyl group-containing low molecular weight compounds such as trimethylolpropane triglycidyl ether, trimethylolphenol triglycidyl ether, and α,α-bis(4-hydroxyphenyl)-4-(4-hydroxy-α,α-dimethylbenzyl)ethylbenzene (TrisP-PA) triglycidyl ether; tetravalent glycidyl group-containing low molecular weight compounds such as pentaerythritol tetraglycidyl ether and tetramethylol bisphenol A tetraglycidyl ether; polyvalent glycidyl group-containing low molecular weight compounds such as dipentaerythritol pentaglycidyl ether and dipentaerythritol hexaglycidyl ether; and glycidyl group-containing high molecular weight compounds such as polyglycidyl(meth)acrylate and a 1,2-epoxy-4-(2-oxiranyl)cyclohexane adduct of 2,2-bis(hydroxymethyl)-1-butanol.

In the crosslinking agent (b) the number of substituents, which comprise a methylol group, an alkoxymethyl group, and an acyloxymethyl group, is 2 to 6 in the case of the melamine compound and 2 to 4 in the case of the glycoluril compound, guanamine compound, or urea compound, and preferably 5 to 6 in the case of the melamine compound and 3 to 4 in the case of the glycoluril compound, guanamine compound, or urea compound.

Hereinafter, the melamine compound, guanamine compound, glycoluril compound, and urea compound related to (b) above are sometimes together called a compound related to (b) (methylol group-containing compound, alkoxymethyl group-containing compound, or acyloxymethyl group-containing compound).

The methylol group-containing compound related to (b) is obtained by heating the foregoing alkoxymethyl group-containing compound related to (b) in an alcohol in the presence of an acid catalyst such as hydrochloric acid, sulfuric acid, nitric acid, or methanesulfonic acid. The acyloxymethyl group-containing compound related to (b) is obtained by mixing, with stirring, the methylol group-containing compound related to (b) and an acyl chloride in the presence of a basic catalyst.

Specific examples of the substituent-containing compounds related to (b) are cited below.

Examples of the melamine compound include hexamethylolmelamine, hexamethoxymethylmelamine, compounds in which one to five methylol groups in hexamethylolmelamine are methoxymethylated or mixtures thereof, hexamethoxyethylmelamine, hexaacyloxymethylmelamine, and compounds in which one to five methylol groups in hexamethylolmelamine are acyloxymethylated or mixtures thereof.

Examples of the guanamine compound include tetramethylolguanamine, tetramethoxymethylguanamine, compounds in which one to three methylol groups in tetramethylolguanmine are methoxymethylated or mixtures thereof, tetramethoxyethylguanamine, tetraacyloxymethylguanamine, and compounds in which one to three methylol groups in tetramethylolguanamine are acyloxymethylated or mixtures thereof.

Examples of the glycoluril compound include tetramethylolglycoluril, tetramethoxymethylglycoluril, compounds in which one to three methylol groups of tetramethyloylglycoluril are methoxymethylated or mixtures thereof, and compounds in which one to three methylol groups in tetramethylolglycoluril are acyloxymethylated or mixtures thereof.

Examples of the urea compound include tetramethylolurea, tetramethoxymethylurea, compounds in which one to three methylol groups in tetramethylolurea are methoxymethylated or mixtures thereof, and tetramethoxyethylurea. The compounds related to (b) may be used singly or as a combination thereof.

The crosslinking agent (c), that is, the phenol compound, naphthol compound or hydroxyanthracene compound, which is substituted with at least one group selected from the group consisting of a methylol group, an alkoxymethyl group, and an acyloxymethyl group, contributes not only to suppressing intermixing with a topcoat photoresist but also to increasing the film strength by thermal crosslinking, in the same way as for the case of the crosslinking agent (b) described above.

Hereinafter, these compounds are sometimes together called a compound related to (c) (methylol group-containing compound, alkoxy methyl group-containing compound, or acyloxymethyl compound).

The number of methylol, alkoxymethyl, and acyloxymethyl groups contained in the crosslinking agent component (c) should be at least two per molecule. Phenolic compounds in which all of the 2- and 4-positions are substituted are preferable from the viewpoints of thermal crosslinking properties and storage stability. Furthermore, as the naphthol compound or hydroxyanthracene compound to serve as the skeleton, compounds in which all of the ortho- and para-positions with respect to the OH group are substituted are preferable.

The phenol compound to serve as the skeleton may be unsubstituted or substituted at the 3- or 5-position thereof. Furthermore, the naphthol compound may be unsubstituted or substituted at positions other than the ortho-position with respect to the OH group.

The methylol group-containing compound related to (c) is obtained by reacting, as the starting material, a compound having a hydrogen atom at the ortho- or para-position (2- or 4-position) with respect to the phenolic OH group with formalin in the presence of a basic catalyst such as sodium hydroxide, potassium hydroxide, ammonia, or a tetraalkylammonium hydroxide. The alkoxymethyl group-containing compound related to (c) is obtained by heating the foregoing methylol group-containing compound related to (c) in an alcohol in the presence of an acid catalyst such as hydrochloric acid, sulfuric acid, nitric acid, or methanesulfonic acid. The acyloxymethyl group-containing compound related to (c) is obtained by reacting the foregoing methylol group-containing compound related to (c) with an acyl chloride in the presence of a basic catalyst.

Examples of the skeleton compound in the crosslinking agent (c) include phenol compounds, naphthol compounds, and hydroxyanthracene compounds in which the ortho- or para-position with respect to the phenolic OH group is unsubstituted, such as phenol, various isomers of cresol, 2,3-xylenol, 2,5-xylenol, 3,4-xylenol, 3,5-xylenol, bisphenols such as bisphenol A, 4,4'-bishydroxybiphenyl, TrisP-PA (manufactured by Honshu Chemical Industry Co., Ltd.), naphthol, dihydroxynaphthalene, and 2,7-dihydroxyanthracene.

Specific examples of the crosslinking agent (c) include trimethylolphenol, tri(methoxymethyl)phenol, compounds in which one or two methylol groups in trimethylolphenol are methoxymethylated, trimethylol-3-cresol, tri(methoxymethyl)-3-cresol, compounds in which one or two methylol groups in trimethylol-3-cresol are methoxymethylated, dimethylolcresols such as 2,6-dimethylol-4-cresol, tetramethylol bisphenol A, tetramethoxymethyl bisphenol A, compounds in which one to three methylol groups of tetramethylol bisphenol A are methoxymethylated, tetramethylol-4,4'-bishydroxybiphenyl, tetramethoxymethyl-4,4'-bishydroxybiphenyl, a hexamethylol compound of TrisP-PA, a hexamethoxymethyl compound of TrisP-PA, compounds in which one to five methylol groups in a hexamethylol compound of TrisP-PA are methoxymethylated, and bishydroxymethylnaphthalenediol.

As the hydroxyanthracene compound, 1,6-dihydroxymethyl-2,7-dihydroxyanthracene may be cited.

Examples of the acyloxymethyl group-containing compound include compounds in which some or all of the methylol groups in the foregoing methylol group-containing compounds are acyloxymethylated.

Among these compounds, trimethylolphenol, bishydroxymethyl-p-cresol, tetramethylol bisphenol A, a hexamethylol compound of TrisP-PA (manufactured by HONSHU CHEMICAL INDUSTRY CO., LTD.), and phenol compounds in which the methylol groups in the foregoing compounds are substituted with an alkoxymethyl group or both a methylol group and an alkoxymethyl group are preferable. These compounds related to (c) may be used singly or in combination.

When a crosslinking agent is contained in the present invention, the total content of the curable compositions (a) to (c) in the curable coloring composition varies depending on the type thereof used, but it is preferably from 1 to 70 weight %, more preferably from 5 to 50 weight %, and particularly preferably from 7 to 30 weight % relative to the total solids content of the composition.

Polymerizable Monomer

The curable coloring composition of the present invention may suitably comprise at least one type of polymerizable monomer. A polymerizable monomer is contained mainly when the curable coloring composition is constituted as negative-working. In addition, it may be contained in a positive-working system comprising a naphthoquinone diazide compound described later, together with a photopolymerization initiator described later, and in this case the degree of curing of a pattern formed may be further promoted.

This polymerizable monomer is useful in terms of achieving higher sensitivity and higher resolution of the curable coloring composition of the present invention by use in combination with a photopolymerization initiator described later. The polymerizable monomer is explained below.

As the polymerizable monomer, ethylenically unsaturated group-containing compounds that have a boiling point of 100° C. or higher at atmospheric pressure are preferable. Examples thereof include monofunctional acrylates or methacrylates such as polyethylene glycol mono(meth)acrylate, polypropylene glycol mono(meth)acrylate, and phenoxyethyl(meth)acrylate; polyfunctional acrylates or methacrylates such as polyethylene glycol di(meth)acrylate, trimethylolethane tri(meth)acrylate, neopentyl glycol di(meth)acrylate, pentaerythritol tri(meth)acrylate, pentaerythritol tetra(meth)acrylate, dipentaerythritol penta(meth)acrylate, dipentaerythritol hexa(meth)acrylate, hexanediol (meth)acrylate, trimethylolpropane tri(acryloyloxypropyl)ether, tri(acryloyloxyethyl) isocyanurate, compounds obtainable by adding ethylene oxide or propylene oxide to a polyfunctional alcohol such as glycerin or trimethylolethane and then (meth)acrylating the resultant adduct, urethane acrylates described in JP-B-48-41708, JP-B-50-6034, and JP-A-51-37193, polyester acrylates described in JP-A-48-64183, JP-B-49-43191, and JP-B-52-30490, and epoxy acrylates obtained as a reaction product between an epoxy resin and (meth)acrylic acid; and mixtures thereof.

In addition, photo-curable monomers and oligomers described in Journal of the Adhesion Society of Japan, Vol. 20, No. 7, pages 300-308 can be cited.

The content of the polymerizable monomer in the curable coloring composition is preferably 0.1 to 90 weight %, more preferably 1.0 to 80 weight %, and particularly preferably 2.0 to 70 weight % relative to the solids content of the composition.

Radiation-Sensitive Compound

The curable coloring composition of the present invention may suitably comprise at least one radiation-sensitive compound.

The radiation-sensitive compound that can be used in the present invention is a compound capable of starting a chemical reaction such as radical generation, acid generation, or base generation upon application of radiation such as UV, deep UV, visible light, IR light, or an electron beam. The radiation-sensitive compound is used for making the above-mentioned alkali-soluble resin insoluble by a reaction such as crosslinking, polymerization, acidic group decomposition, etc. or making a coated film insoluble in an alkali developer by causing polymerization of a polymerizable monomer or oligomer present in the coated film, crosslinking of a crosslinking agent, etc.

This radiation-sensitive compound is useful from the viewpoint of achieving higher sensitivity and higher resolution of the curable coloring composition of the present invention.

A photopolymerization initiator is preferably contained in the curable coloring composition when the curable coloring composition is a negative-type composition, while a naphthoquinone diazide compound is contained when the curable coloring composition is a positive-working composition.

Photopolymerization initiator, etc.

The photopolymerization initiator used in the case of a negative-working system is described first. The photopolymerization initiator is not particularly limited as long as the photopolymerization initiator can polymerize the polymerizable monomer (polymerizable group-containing monomer), and is selected preferably from the viewpoints of characteristics, initiation efficiency, absorption wavelength, availability, cost, etc. A positive-working system containing a naphthoquinone diazide compound may further contain a photopolymerization initiator, which further enhances the degree of curing of the pattern obtained.

As the photopolymerization initiator there can be cited at least one active halogen compound selected from halomethyloxadiazole compounds and halomethyl-s-triazine compounds, a 3-aryl substituted coumarin compound, a lophine dimer, a benzophenone compound, an acetophenone compound and a derivatives thereof, a cyclopentadiene-benzene-iron complex and a salt thereof, and an oxime compound.

Examples of the halomethyloxadiazole compounds, which are active halogen compounds, include 2-halomethyl-5-vinyl-1,3,4-oxadiazole compounds, etc. described in JP-B-57-6096; 2-trichloromethyl-5-styryl-1,3,4-oxadiazole, 2-trichloromethyl-5-(p-cyanostyryl)-1,3,4-oxadiazole, and 2-trichloromethyl-5-(p-methoxystyryl)-1,3,4-oxadiazole.

Examples of the halomethyl-s-triazine compounds, which are active halogen compounds, include vinyl-halomethyl-s-triazine compounds described in JP-B-59-1281, 2-(naphth-1-yl)-4,6-bishalomethyl-s-triazine compounds described in JP-A No. 53-133428; and 4-(p-aminophenyl)-2,6-dihalomethyl-s-triazine compounds.

Other specific examples thereof include 2,4-bis(trichloromethyl)-6-p-methoxystyryl-s-triazine, 2,6-bis(trichloromethyl)-4-(3,4-methylenedioxyphenyl)-1,3,5-triazine, 2,6-bis(trichloromethyl)-4-(4-methoxyphenyl)-1,3,5-triazine, 2,4-bis(trichloromethyl)-6-(1-p-dimethylaminophenyl-1,3-butadienyl)-s-triazine, 2-trichloromethyl-4-amino-6-p-methoxystyryl-s-triazine, 2-(naphth-1-yl)-4,6-bis(trichloromethyl)-s-triazine, 2-(4-methoxynaphth-1-yl)-4,6-bis(trichloromethyl)-s-triazine, 2-(4-ethoxynaphth-1-yl)-4,6-bis(trichloromethyl)-s-triazine, 2-(4-butoxynaphth-1-yl)-4,6-bis(trichloromethyl)-s-triazine, 2-[4-(2-methoxyethyl)naphth-1-yl]-4,6-bis(trichloromethyl)-s-triazine, 2-[4-(2-ethoxyethyl)naphth-1-yl]-4,6-bis(trichloromethyl)-s-triazine, 2-[4-(2-butoxyethyl)naphth-1-yl]-4,6-bis(trichloromethyl)-s-triazine, 2-(2-methoxynaphth-1-yl)-4,6-bis(trichloromethyl)-s-triazine, 2-(6-methoxy-5-methylnaphth-2-yl)-4,6-bis(trichloromethyl)-s-triazine, 2-(6-methoxynaphth-2-yl)-4,6-bis(trichloromethyl)-s-triazine, 2-(5-methoxynaphth-1-yl)-4,6-bis(trichloromethyl)-s-triazine, 2-(4,7-dimethoxynaphth-1-yl)-4,6-bis(trichloromethyl)-s-triazine, 2-(6-ethoxynaphth-2-yl)-4,6-bis(trichloromethyl)-s-triazine, 2-(4,5-dimethoxynaphth-1-yl)-4,6-bis(trichloromethyl)-s-triazine, 4-[p-N,N-di(ethoxycarbonylmethyl)aminophenyl]-2,6-di (trichloromethyl)-s-triazine, 4-[o-methyl-p-N,N-di(ethoxycarbonylmethyl)aminophenyl]-2,6-di(trichloromethyl)-s-triazine, 4-[p-N,N-di(chloroethyl)aminophenyl]-2,6-di(trichloromethyl)-s-triazine, 4-[o-methyl-p-N,N-di(chloroethyl)aminophenyl]-2,6-di(trichloromethyl)-s-triazine, 4-(p-N-chloroethylaminophenyl)-2,6-di(trichloromethyl)-s-triazine, 4-(p-N-ethoxycarbonylmethylaminophenyl)-2,6-di(trichloromethyl)-s-triazine, 4-[p-N,N-di(phenyl)aminophenyl]-2,6-di(trichloromethyl)-s-triazine, 4-(p-N-chloroethylcarbonylaminophenyl)-2,6-di(trichloromethyl)-s-triazine, 4-[p-N-(p-methoxyphenyl)carbonylaminophenyl]-2,6-di(trichloromethyl)-s-triazine, 4-[m-N,N-di(ethoxycarbonylmethyl)aminophenyl]-2,6-di(trichloromethyl)-s-triazine, 4-[m-bromo-p-N,N-di(ethoxycarbonylmethyl)aminophenyl]-2,6-di(trichloromethyl)-s-triazine, 4-[m-chloro-p-N,N-di(ethoxycarbonylmethyl)aminophenyl]-2,6-di(trichloromethyl)-s-triazine, 4-[m-fluoro-p-N,N-di(ethoxycarbonylmethyl)aminophenyl]-2,6-di(trichloromethyl)-s-triazine, 4-[o-bromo-p-N,N-di(ethoxycarbonylmethyl)aminophenyl]-2,6-di(trichloromethyl)-s-triazine, 4-[o-chloro-p-N,N-di(ethoxycarbonylmethyl)aminophenyl-2,6-di(trichloromethyl)-s-triazine, 4-[o-fluoro-p-N,N-di(ethoxycarbonylmethyl)aminophenyl]-2,6-di(trichloromethyl)-s-triazine, 4-[o-bromo-p-N,N-di(chloroethyl)aminophenyl]-2,6-di(trichloromethyl)-s-triazine, 4-[o-chloro-p-N,N-di(chloroethyl)aminophenyl]-2,6-di(trichloromethyl)-s-triazine, 4-[m-fluoro-p-N,N-di(chloroethyl)aminophenyl]-2,6-di(trichloromethyl)-s-triazine, 4-[m-bromo-p-N,N-di(chloroethyl)aminophenyl]-2,6-di(trichloromethyl)-s-triazine, 4-[m-chloro-p-N,N-di(chloroethyl)aminophenyl]-2,6-di(trichloromethyl)-s-triazine, 4-[m-fluoro-p-N,N-di(chloroethyl)aminophenyl]-2,6-di(trichloromethyl)-s-triazine, 4-(m-bromo-p-N-ethoxycarbonylmethylaminophenyl)-2,6-di(trichloromethyl)-s-triazine, 4-(m-chloro-p-N-ethoxycarbonylmethylaminophenyl)-2,6-di(trichloromethyl)-s-triazine, 4-(m-fluoro-p-N-ethoxycarbonylmethylaminophenyl)-2,6-di(trichloromethyl)-s-triazine, 4-(o-bromo-p-N-ethoxycarbonylmethylaminophenyl)-2,6-di(trichloromethyl)-s-triazine, 4-(o-chloro-p-N-ethoxycarbonylmethylaminophenyl)-2,6-di(trichloromethyl)-s-triazine, 4-(o-fluoro-p-N-ethoxycarbonylmethylaminophenyl)-2,6-di(trichloromethyl)-s-triazine, 4-(m-bromo-p-N-chloroethylaminophenyl)-2,6-di(trichloromethyl)-s-triazine, 4-(m-chloro-p-N-chloroethylaminophenyl)-2,6-di(trichloromethyl)-s-triazine, 4-(m-fluoro-p-N-chloroethylaminophenyl)-2,6-di(trichloromethyl)-s-triazine, 4-(o-bromo-p-N-chloroethylaminophenyl)-2,6-di(trichloromethyl)-s-triazine, 4-(o-chloro-p-N-chloroethylaminophenyl)-2,6-di(trichloromethyl)-s-triazine, and 4-(o-fluoro-p-N-chloroethylaminophenyl)-2,6-di(trichloromethyl)-s-triazine.

Other useful examples thereof include the TAZ series TAZ-107, TAZ-110, TAZ-104, TAZ-109, TAZ-140, TAZ-204, TAZ-113, and TAZ-123 manufactured by Midori Kagaku Co., Ltd.; the T series T-OMS, T-BMP, T-R, and T-B manufactured by PANCHIM; the IRGACURE series IRGACURE 369, IRGACURE 784, IRGACURE 651, IRGACURE 184, IRGACURE 500, IRGACURE 1000, IRGACURE 149, IRGACURE 819, and IRGACURE 261 manufactured and the DAROCUR series DAROCUR 1173 manufactured by Ciba Specialty Chemicals; 4,4-bis(diethylamino)benzophenone, 2-(O-benzoyloxime)-1-[4-(phenylthio)phenyl]-1,2-octanedione, 2-benzyl-2-dimethylamino-4-morpholinobutyrophenone, 2,2-dimethoxy-2-phenylacetophenone, 2-(o-chlorophenyl)-4,5-diphenylimidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2-(p-dimethoxyphenyl)-4,5-diphenylimidazolyl dimer, 2-(2,4-dimethoxyphenyl)-4,5-diphenylimidazolyl dimer, 2-(p-methylmercaptophenyl)-4,5-diphenylimidazolyl dimer, and benzoin isopropyl ether.

In addition to the photopolymerization initiators described above, the curable coloring composition of the present invention may contain other known photopolymerization initiators. Specific examples thereof include vicinal polyketaldonyl compounds described in U.S. Pat. No. 2,367,660; α-carbonyl compounds described in U.S. Pat. Nos. 2,367,661 and 2,367,670; acyloin ethers described in U.S. Pat. No. 2,448,828; α-hydrocarbon-substituted aryl acyloin compounds described in U.S. Pat. No. 2,722,512; polynuclear quinone compounds described in U.S. Pat. Nos. 3,046,127 and 2,951,758; a combination of triallylimidazole dimer and p-aminophenyl ketone described in U.S. Pat. No. 3,549,367; and benzothiazole compounds and trihalomethyl-s-triazine compounds described in JP-B-51-48516.

The content of photopolymerization initiator in the curable coloring composition is preferably 0.01 to 50 weight %, more preferably 1 to 30 weight %, and particularly preferably 1 to 20 weight % with respect to the solids content (weight) of the polymerizable monomer. When the content is at least 0.01 weight % the polymerizability is excellent, and when the content is no greater than 50 weight % the molecular weight increases and the film strength is excellent.

The photopolymerization initiator may be used in combination with a sensitizer or a photostabilizer.

Specific examples thereof include benzoin, benzoin methyl ether, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-anthraquinone, 2,6-dichloro-9,10-anthraquinone, xanthone, 2-methylxanthone, 2-methoxyxanthone, 2-ethoxyxanthone, thioxanthone, 2,4-diethylthioxanthone, acridone, 10-butyl-2-chloroacridone, benzil, dibenzalacetone, p-(dimethylamino)phenyl styryl ketone, p-(dimethylamino)phenyl p-methylstyryl ketone, benzophenone, p-(dimethylamino)benzophenone (or Michler's ketone), p-(diethylamino)benzophenone, benzanthrone, benzothiazole compounds, etc. described in JP-B-51-48516, and TINUVIN 1130 and 400.

Other than those mentioned above, a thermal polymerization inhibitor is preferably added and, for example, a hydroquinone, p-methoxyphenol, di-t-butyl-p-cresol, pyrogallol, t-butylcatechol, benzoquinone, 4,4-thiobis(3-methyl-6-t-butylphenol), 2,2-methylenebis(4-methyl-6-t-butylphenol), 2-mercaptobenzoimidazole, etc. are useful.

(Naphthoquinone Diazide Compound)

The naphthoquinone diazide compound, which is used in formation of a positive-working system, is now explained.

The naphthoquinone diazide compound is a compound having at least one o-quinone diazide group, and specific examples thereof include an o-naphthoquinone diazide-5-sulfonic acid ester, an o-naphthoquinone diazide-5-sulfonamide, an o-naphthoquinone diazide-4-sulfonic acid ester, and an o-naphthoquinone diazide-4-sulfonamide. These ester and amide compounds can be prepared, for example, by a known method using a phenol compound represented by Formula (1) described in JP-A-2-84650 or JP-A-3-49437.

It is preferable that when the curable coloring composition is used for a positive-working system, the binder and the crosslinking agent are usually dissolved in an organic solvent at approximately 2 to 50 weight % and approximately 2 to 30 weight % respectively. It is preferable that the naphthoquinone diazide compound and the dye described above are usually added at approximately 2 to 30 weight % and approximately 2 to 50 weight % respectively to the solution containing the binder and the cross linking agent.

Solvent

In preparation of the curable coloring composition of the present invention, a solvent may generally be contained. The solvent is basically not particularly limited as long as it satisfies requirements in terms of the solubility of respective components and the coating properties of the curable coloring composition, and is preferably selected taking into consideration the solubility of the binder, coating properties, and stability in particular.

Specific examples of the solvent include esters such as ethyl acetate, n-butyl acetate, isobutyl acetate, amyl formate, isoamyl acetate, isobutyl acetate, butyl propionate, isopropyl butyrate, ethyl butyrate, butyl butyrate, alkyl esters, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, and ethyl ethoxyacetate; alkyl 3-oxypropionate esters such as methyl oxypropionate and ethyl 3-oxypropionate, for example methyl 3-methoxypropionate, ethyl 3-methoxypropionate, methyl 3-ethoxypropionate, and ethyl 3-ethoxypropionate; alkyl 2-oxypropionate esters such as methyl 2-oxypropionate, ethyl 2-oxypropionate, and propyl 2-oxypropionate, for example methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate, and ethyl 2-ethoxy-2-methylpropionate; methyl pyruvate, ethyl pyruvate, propyl pyruvate, methyl acetoacetate, ethyl acetoacetate, methyl 2-oxobutanoate, and ethyl 2-oxobutanoate;

ethers such as diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol methyl ether, propylene glycol monomethyl ether acetate, propylene glycol ethyl ether acetate, and propylene glycol propyl ether acetate; ketones such as methyl ethyl ketone, cyclohexanone, 2-heptanone, and 3-heptanone; and aromatic hydrocarbons such as toluene and xylene.

Among them, more preferable are methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethylcarbitol acetate, butylcarbitol acetate, propylene glycol methyl ether, propylene glycol monomethyl ether acetate, etc.

Various Additives

The curable coloring composition of the present invention may contain, as necessary, various additives such as fillers, polymeric compounds other than those described above, surfactants, adhesion promoters, antioxidants, ultraviolet absorbents, aggregation inhibitors, etc. Examples thereof include additives described in paragraphs 0274 to 0276 of JP-A-2008-292970.

Specific examples of the various additives include fillers such as glass and alumina; polymeric compounds other than the binder resin, such as polyvinylalcohol, polyacrylic acid, polyethylene glycol monoalkyl ethers, and polyfluoroalkyl acrylates; surfactants such as nonionic, cationic, and anionic surfactants; adhesion promoters such as vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, and 3-mercaptopropyltrimethoxysilane; antioxidants such as 2,2-thiobis(4-methyl-6-t-butylphenol) and 2,6-di-t-butylphenol; ultraviolet absorbents such as 2-(3-t-butyl-5-methyl-2-hydroxyphenyl)-5-chlorobenzotriazole and alkoxybenzophenones; and aggregation inhibitors such as sodium polyacrylate.

In addition, an organic carboxylic acid, preferably a low molecular weight organic carboxylic acid having a molecular weight of no greater than 1,000, may be added to the composition, for promoting the alkali solubility of a region that has not been cured and improvement of the development properties of the curable coloring composition of the present invention.

Specific examples thereof include fatty monocarboxylic acids such as formic acid, acetic acid, propionic acid, butyric acid, valeric acid, pivalic acid, caproic acid, diethylacetic acid, enanthic acid, and caprylic acid; fatty dicarboxylic acids such as oxalic acid, malonic acid, succinic acid, glutaric acid, adipic acid, pimelic acid, suberic acid, azelaic acid, sebacic acid, brassylic acid, methylmalonic acid, ethylmalonic acid, dimethylmalonic acid, methylsuccinic acid, tetramethylsuccinic acid, and citraconic acid; aliphatic tricarboxylic acids such as tricarballylic acid, aconitic acid, and camphoronic acid; aromatic monocarboxylic acids such as benzoic acid, toluic acid, cuminic acid, hemellitic acid, and mesitylenic acid; aromatic polycarboxylic acids such as phthalic acid, isophthalic acid, terephthalic acid, trimellitic acid, trimesic acid, mellophanic acid, and pyromellitic acid; and other carboxylic acids such as phenylacetic acid, hydratropic acid, hydrocinnamic acid, mandelic acid, phenylsuccinic acid, atropic acid, cinnamic acid, methyl cinnamate, benzyl cinnamate, cinnamylideneacetic acid, coumaric acid, and umbellic acid.

The curable coloring composition of the present invention may be suitably used for forming color pixels such as those of a color filter used for a liquid crystal display (LCD) or a solid-state image sensor (such as a CCD or CMOS), or for producing a printing ink, an inkjet ink, or a paint.

<Color Filter and Method for Producing Same>

The color filter of the present invention is now explained in detail by way of a method for producing same.

The color filter of the present invention is a color filter that is obtained by curing the curable coloring composition of the present invention, and is preferably a color filter produced by the production method below.

In the method for producing a color filter of the present invention, the above-mentioned curable coloring composition of the present invention is used. The color filter of the present invention may most suitably be produced by coating a support with the above-mentioned curable coloring composition of the present invention by a coating method involving spin coating, cast coating, roll coating, etc. to thus form a radiation-sensitive composition layer, imagewise exposing the layer through, for example, a predetermined mask pattern, and developing using a developer so as to form a negative-working or positive-working colored pattern (image formation step). In this process, a curing step of curing the colored pattern thus formed by heating and/or exposing may be provided as necessary. As light or radiation used here, UV such as g rays, h rays, or i rays is particularly preferably used. Furthermore, when the curable coloring composition is of a positive-working system, a step of post-baking the colored pattern after the image formation step may be provided.

A color filter may be produced with a required number of hues by repeating the image formation step (and the curing step as necessary) according to a required number of hues in the case of negative-working, and by repeating the image formation step and the post-baking according to a required number of hues in the case of positive-working.

Furthermore, imagewise exposure involving scanning with laser light may also be employed.

Examples of the support include soda glass, Pyrex (registered trademark) glass, quartz glass, glass having a transparent conductive film adhered thereto, and a substrate for a photoelectric transducer used in an image sensor, etc., such as a silicon substrate or a complementary metal oxide semiconductor (CMOS). On these substrates, black stripes may be formed so as to isolate pixels from each other.

Furthermore, an undercoat layer may be optionally disposed on the support in order to improve the adhesion to an upper layer, to prevent diffusion of a substance, or to flatten a substrate surface.

As the developer used for the method of producing a color filter of the present invention, any composition may be used as long as it dissolves an area that is to be developed and removed (for example, an uncured area in the case of negative-working) of the curable coloring composition of the present invention but does not dissolve a cured area that constitutes a filter. Specifically, a combination of various organic solvents or an alkaline aqueous solution may be used.

As the organic solvent, the foregoing solvents used during preparation of the curable coloring composition of the present invention can be cited.

As the alkaline aqueous solution, for example, an alkaline aqueous solution is suitably used in which an alkaline compound such as sodium hydroxide, potassium hydroxide, sodium carbonate, sodium silicate, sodium metasilicate, aqueous ammonia, ethylamine, diethylamine, dimethylethanolamine, tetramethylammonium hydroxide, tetraethylammonium hydroxide, choline, pyrrole, piperidine, or 1,8-diazabicyclo[5.4.0]-7-undecene is dissolved at a concentration of preferably 0.001 to 10 weight %, and more preferably 0.01 to 1 weight %. In the case where a developer containing such an alkaline aqueous solution is used, washing with water is usually carried out after development.

The color filter of the present invention can be used for liquid crystal displays or solid-state image sensors such as CCDs, and is particularly suitable for a high resolution CCD device or CMOS device that has more than 1,000,000 pixels. The color filter of the present invention may be used for example as a color filter by being disposed between a light-receiving portion of respective pixels that constitute a CCD and a light-condensing micro lens.

In accordance with the present invention, there can be provided a curable coloring composition that has good color hue, high transmittance properties, high light fastness and heat fastness, and excellent stability over time and solvent resistance after curing, a color filter that has good color hue, high transmittance properties, and excellent light fastness, heat fastness, and solvent resistance, and is compatible with high resolution, and a method for producing same.

EXAMPLES

The present invention will be more specifically described below with reference to Examples, but the present invention is not limited to the Examples below as long as the scope thereof is maintained. In addition, the term 'parts' is on the basis of weight unless otherwise indicated.

Example 1

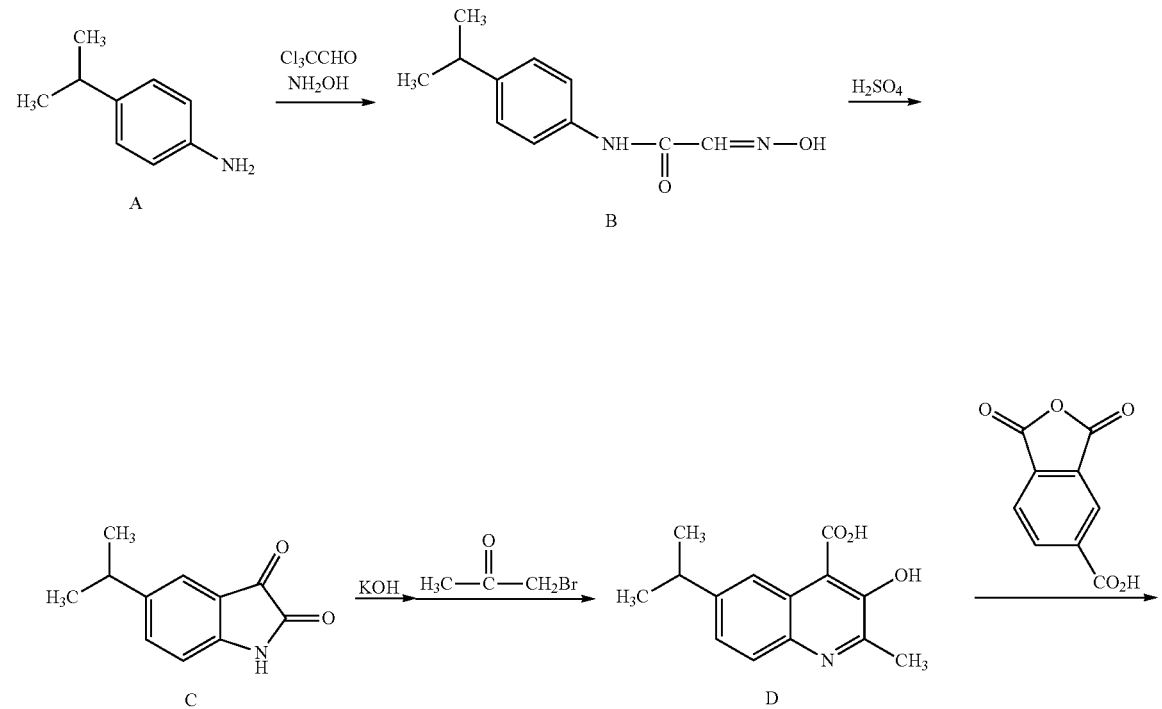

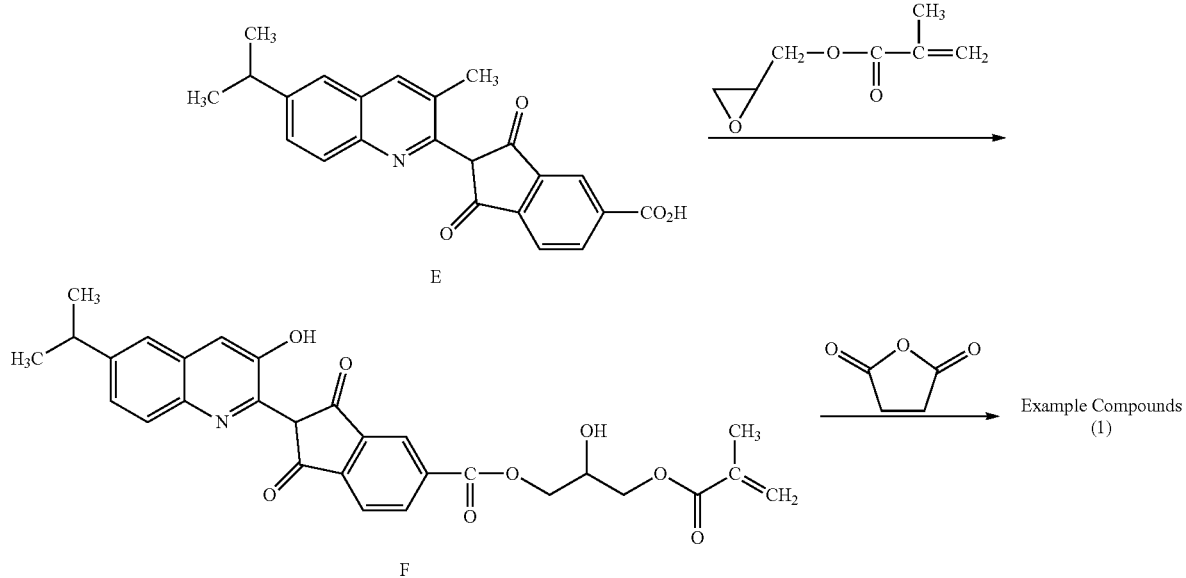

E

F

<Preparation of Intermediate B>

A 5 L three-necked flask equipped with an alkali trap was charged with 64.8 g (0.479 mol) of 4-isopropylaniline, 48 mL of conc. hydrochloric acid, and 360 mL of water, and stirring was carried out at room temperature. A solution of 95.0 g (0.574 mol) of chloral hydrate and 500 g of sodium sulfate dissolved in 1,500 mL of water was added thereto dropwise, and a solution of hydroxylamine monohydrate dissolved in 500 mL of water was further added thereto dropwise. A reaction was carried out under a nitrogen atmosphere at 100° C. for 12 hours, and the mixture was cooled to room temperature. Crystals were separated by filtration, thus giving 98.0 g of intermediate B as a pale brown solid (yield 99%). MS (m/z)=207 ([M+1]$^+$, 100%).

<Preparation of Intermediate C>

A 2,000 mL three-necked flask was charged with 800 mL of conc. sulfuric acid and water cooled, and 200 g (0.97 mol) of intermediate B was added thereto portionwise over 60 minutes. After a reaction was carried out at 70° C. to 80° C. for 30 minutes, the reaction mixture was water cooled and added carefully dropwise at a temperature of 15° C. or below to 6,000 g of iced water while stirring. After stirring was carried out at an internal temperature of 15° C. for 30 minutes, a precipitated solid was filtered and washed with water, thus giving 170 g of intermediate C as a solid (yield 90%). MS (m/z)=189 (M$^+$, 100%).

<Preparation of Intermediate D>

A 1,000 mL three-necked flask was charged with 46 g (0.243 mole) of intermediate C, 97 mL of water, and 97 g of potassium hydroxide, and stirring was carried out at room temperature for 30 minutes. 242 mL of toluene, 1 g of tetraethylammonium bromide, and 50 g (0.364 mol) of bromoacetone were further added thereto, and a reaction was carried out at 60° C. for 2 hours. The reaction mixture was cooled to room temperature, the toluene layer was removed, and the aqueous layer was washed with ethyl acetate. The aqueous layer thus washed was cooled to 15° C. or below, and an appropriate amount of conc. hydrochloric acid was added thereto to thus precipitate crystals. The crystals were separated by filtration and recrystallized from isopropyl alcohol, thus giving 12.3 g of intermediate D as yellow crystals (yield 21%). MS (m/z)=246 ([M+1]$^+$, 100%).

<Preparation of Intermediate E>

A 1,000 mL three-necked flask was charged with 84.5 g (0.44 mol) of trimellitic anhydride and 400 mL of sulfolane, and the internal temperature was increased to 185° C. 98.0 g (0.40 mol) of intermediate D was added thereto portionwise slowly while taking care with the carbon dioxide generated. A reaction was carried out at 200° C. for 2 hours, the reaction mixture was cooled to room temperature, and 200 mL of methanol was added. The reaction mixture was stirred at room temperature, and crystals were separated by filtration and washed with methanol, thus giving 91 g of intermediate F as orange crystals (yield 55%). MS (m/z)=375 (M$^+$, 100%).

<Preparation of Intermediate F>

A 1,000 mL three-necked flask was charged with 50 g (0.133 mol) of intermediate E, 500 mL of N-methyl-2-pyrrolidone (NMP), 5.6 g tetraethylammonium bromide, 100 mg of 4-hydroxy-1,1,2,2-tetramethylpiperidine-N-oxide, and 19 g (0.133 mol) of glycidyl methacrylate, and a reaction was carried out at 130° C. for 2 hours. The reaction mixture was cooled to room temperature, added dropwise to 3,000 mL of water, and allowed to stand overnight. Crystals thus precipitated were separated by filtration and washed well with water, and the crude crystals thus obtained were recrystallized from 450 mL of acetonitrile, thus giving 46.1 g of intermediate F comprising isomers (yield 67%).

<Synthesis of Example Compounds (1) and (2)>

A 200 mL three-necked flask was charged with 10 g (0.0193 mol) of intermediate F comprising isomers, 100 mL of toluene, 5.0 g of succinic anhydride, 2.06 g of pyridine, and 1 mL of nitrobenzene, and a reaction was carried out at 80° C. for 6 hours. The reaction mixture was cooled, and the crystals were separated by filtration and washed with n-hexane. The crude crystals thus obtained were subjected to silica gel column chromatography, thus isolating 3.3 g (yield 27%) of example compound (1) and 0.9 g (yield 8%) of example compound (2).

Example compound (1): MS (m/z)=617 (M$^+$, 100%). Absorption spectrum of example compound in ethyl acetate was 444 nm.

Example compound (2): MS (m/z)=617 (M+, 100%). Absorption spectrum of example compound in ethyl acetate was 444.2 nm.

<Synthesis of Example Compounds (3), (4), (9), (10), (29), and (30)>

Example compounds (3), (4), (9), (10), (29), and (30) were synthesized by a method in accordance with the above-mentioned synthesis example.

Example compounds other than example compounds (1), (2), (3), (4), (9), (10), (29), and (30) can also be synthesized by a method in accordance with the above-mentioned synthesis example from a chemical point of view.

<Evaluation>

The maximum absorption wavelengths in the absorption spectra of the example compounds (1), (2), (3), (4), (9), (10), (29), and (30) obtained above (dyes (1), (2), (3), (4), (9), (10), (29), and (30)) in ethyl acetate solution (concentration $1 \times 10^{-6}$ mol/L, optical path length 10 mm) are shown in Table 8 below.

Furthermore, a solution transmission spectrum of example compound (1) (dye (1)) synthesized in Example 1 is shown FIG. 1.

TABLE 8

| Dye | Maximum absorption wavelength (nm) |
| --- | --- |
| (1) | 444.0 |
| (2) | 444.2 |
| (3) | 444.2 |
| (4) | 444.1 |
| (9) | 445.1 |
| (10) | 442.2 |
| (29) | 441.9 |
| (30) | 442.1 |

Example 2

(1) Preparation of Resist Solution A (Negative-Working)

| | |
| --- | --- |
| Propylene glycol monomethyl ether acetate (PGMEA) | 5.20 parts |
| Cyclohexanone | 52.6 parts |
| Binder | 30.5 parts |
| 41% cyclohexanone solution of (benzyl methacrylate/ methacrylic acid/2-hydroxyethyl methacrylate) copolymer (molar ratio = 60:20:20) | |
| Dipentaerythritol hexaacrylate | 10.2 parts |
| Polymerization inhibitor (p-methoxyphenol) | 0.006 parts |
| Fluorine-based surfactant | 0.80 parts |
| (product name: F-475, Dainippon Ink and Chemicals, Incorporated), and | |
| Photopolymerization initiator TAZ-107 (Midori Kagaku Co., Ltd.) | 0.58 parts | were mixed and dissolved, thus preparing resist solution A.

(2) Preparation of Undercoat Layer-Equipped Glass Substrate

A glass substrate (Corning 1737) was subjected to ultrasound washing using 0.5% aqueous NaOH, then washed with water, and subjected to dehydration baking (200° C./20 min). Subsequently, the glass substrate was coated with resist solution A obtained in (1) above using a spin coater so as to give a film thickness of 2 μm and thermally dried at 220° C. for 1 hour, thus giving a cured coating (undercoat layer).

(3) Preparation of Resist Solution B (Negative-Working)

| | |
| --- | --- |
| Cyclohexanone | 80 parts |
| Dipentaerythritol hexaacrylate | 14.0 parts |
| Polymerization inhibitor (p-methoxyphenol) | 0.006 parts |
| Fluorine-based surfactant | 0.80 parts |
| (product name: F-475, Dainippon Ink and Chemicals, Incorporated) | |
| Photopolymerization initiator TAZ-107 (Midori Kagaku Co., Ltd.) | 2.0 parts, and |
| Example compound (1) of the present invention | 4.0 parts | were mixed and dissolved, thus preparing a dye resist solution (curable coloring composition solution (negative-working)).

(4) Exposure and Development (Image Formation) of Resist

The undercoat layer of the undercoat layer-equipped glass substrate obtained in (2) above was coated with the dye resist solution obtained in (3) above using a spin coater so as to give a film thickness of 0.6 μm, and pre-baking was carried out at 100° C. for 120 seconds.

Subsequently, the coated film was exposed using exposure equipment with a wavelength of 365 nm through a mask having a line width of 2 μm at an exposure of 200 mJ/cm². After exposure, development was carried out at 25° C. for 40 seconds using a CD-2000 developer (FUJIFILM Electronic Materials Co., Ltd.). Subsequently, rinsing was carried out with running water for 30 seconds followed by spray drying. Subsequently, post-baking was carried out at 200° C. for 15 minutes.

As hereinbefore described, a pattern suitable as a yellow color constituting a color filter was obtained.

Figure 2:
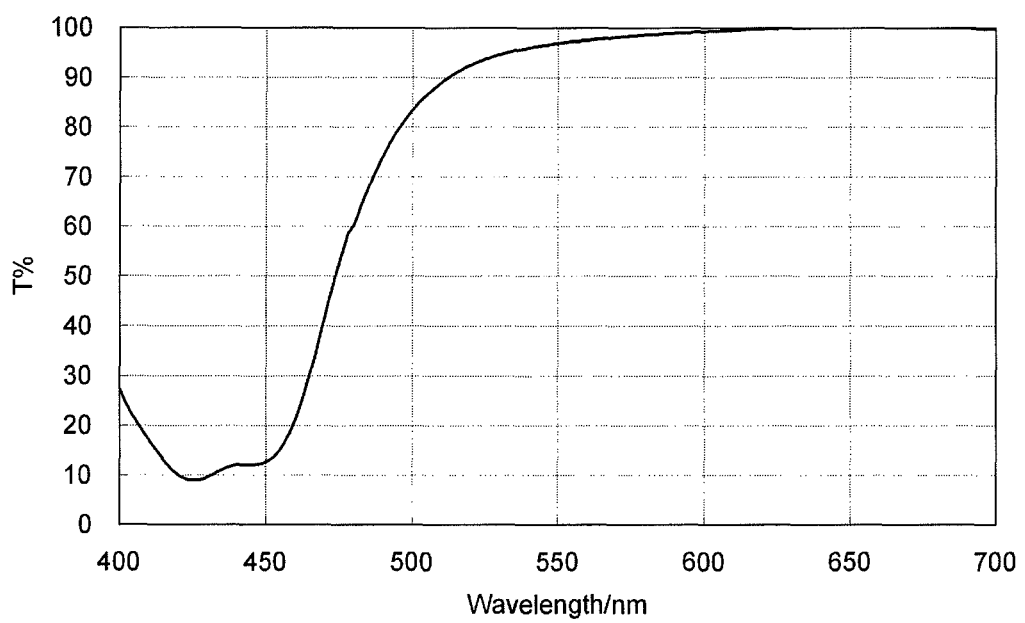
FIG. 2 is a transmission spectrum of a color filter prepared in Example 2.

FIG. 2 shows a transmission spectrum of the color filter prepared in Example 2.

(5) Evaluation

Storage stability over time of the dye resist solution prepared above, and heat fastness, light fastness, solvent resistance, and pattern shape of the coated film provided on the glass substrate using the dye resist solution were evaluated as follows. Evaluation results are shown in Table 9 below.

Storage Stability Over Time

After the dye resist solution was stored at room temperature for 1 month, the degree of deposition of foreign matter in the solution was visually evaluated in accordance with the evaluation criteria below.

—Evaluation Criteria—

Good: deposition was not observed.

Fair: slight deposition was observed.

Poor: deposition was observed.

Heat Fastness

After the glass substrate coated with the dye resist solution was placed on a hot plate at 200° C. so that the substrate face was in contact, and heated for 1 hour, the color difference (ΔEab value) between that before and that after heating was measured using an MCPD-1000 colorimeter (Otsuka Electronics Co., Ltd.) and used as an index for evaluating heat fastness, and evaluation was made in accordance with the evaluation criteria below.

With regard to the ΔEab value, the smaller the value, the better the heat fastness.

—Evaluation Criteria—

Good: ΔEab value<5

Fair: 5≦ΔEab value≦10

Poor: ΔEab value>10

Light Fastness

After the glass substrate coated with the dye resist solution was exposed using a xenon lamp at 100,000 lux for 20 hours (corresponding to 2,000,000 lux·h), the color difference (ΔEab value) between that before and that after exposure was measured and used as an index for evaluating light fastness, and evaluation was made in accordance with the evaluation criteria below.

With regard to the ΔEab value, the smaller the value, the better the light fastness.

—Evaluation Criteria—
Good: ΔEab value<3
Fair: 3≦ΔEab value≦10
Poor: ΔEab value>10

Solvent Resistance

Spectra of various coated films after post-baking obtained in (4) above were measured (spectrum A). These coated films were coated with resist solution A obtained in (1) above at a film thickness of 1 μm and pre-baked, then developed at 23° C. for 120 seconds using a CD-2000 developer (FUJIFILM Electronic Materials Co., Ltd.), and subjected to remeasurement of the spectrum (spectrum B). The proportion of dye remaining (%) was calculated from the difference between these spectra A and B, and this was used as an index for evaluating solvent resistance. The closer to 100% this value, the better the solvent resistance.

Pattern Shape

The developed pattern of various coated films after post-baking obtained in (4) above was examined using an optical microscope (RX-20 digital microscope, Olympus Corporation), and an evaluation of whether or not a fine pattern had been formed was carried out in accordance with the evaluation criteria below.

—Evaluation Criteria—
Good: a fine pattern could be prepared.
Fair: a pattern could be prepared, but the edge of the pattern was not fine.
Poor: a pattern could not be prepared.

Examples 3 to 10

A pattern was formed in the same manner as in Example 2 except that changes to the dye related to the present invention were made in (3) preparation of dye resist solution in Example 2 (however, the weight was the same), and an evaluation was carried out in the same manner. The evaluation results are shown in Table 9 below.

Comparative Examples 1 to 6

A pattern was formed in the same manner as in Example 2 except that changes to Comparative dyes 1 to 6 (Comparative Examples 1 to 6) were made in (4) preparation of dye resist solution of Example 1 (however, the weight was the same), and an evaluation was carried out in the same manner. The evaluation results are shown in Table 9 below together with the results of the Examples.

TABLE 9

| Example No. | Dye | Storage stability over time | Heat fastness | Light fastness | Solvent resistance | Pattern shape |
|---|---|---|---|---|---|---|
| Example 2 | (1) | Good | Good | Good | 97% | Good |
| Example 3 | (5) | Good | Good | Good | 99% | Good |
| Example 4 | (9) | Good | Good | Good | 98% | Good |
| Example 5 | (29) | Good | Good | Good | 93% | Good |
| Example 6 | (30) | Good | Good | Good | 94% | Good |
| Example 7 | (44) | Good | Good | Good | 97% | Good |
| Example 8 | (55) | Good | Good | Good | 92% | Good |
| Example 9 | (56) | Good | Good | Good | 88% | Good |
| Example 10 | (62) | Good | Good | Good | 87% | Good |
| Comp. Ex. 1 | Comparative dye 1 | Poor | Poor | Poor | 45% | Good |
| Comp. Ex. 2 | Comparative dye 2 | Poor | Poor | Poor | 42% | Good |
| Comp. Ex. 3 | Comparative dye 3 | Good | Good | Good | 88% | Poor |
| Comp. Ex. 4 | Comparative dye 4 | Good | Good | Fair | 91% | Fair |
| Comp. Ex. 5 | Comparative dye 5 | Fair | Good | Good | 89% | Fair |
| Comp. Ex. 6 | Comparative dye 6 | Good | Good | Good | 60% | Good |

As shown in Table 9, compared with Comparative Examples 1 and 2, in the Examples, in which the dye related to the present invention was used, all of the dye resist solutions (curable coloring compositions) prepared in solution form had excellent storage stability over time, and the patterns formed using the curable coloring compositions exhibited good heat fastness, light fastness, and solvent resistance.

As shown in Table 9, in Comparative Example 3, in which a quinophthalone dye having an ethylenically unsaturated group but not having a carboxyl group was used, a fine pattern could not be formed.

As shown in Table 9, in Comparative Example 4, in which a quinophthalone dye not having an ethylenically unsaturated group but having a carboxyl group was used, the solvent resistance was not sufficient.

As shown in Table 9, in Comparative Examples 4 and 5, in which a quinophthalone dye having an ethylenically unsaturated group and having a carboxyl group, relatively excellent performance was shown, but although a pattern could be formed, it was rather inadequate.

As shown in Table 9, in Examples 1 to 10, in which, among quinophthalone dyes having an ethylenically unsaturated group and having a carboxyl group, a curable coloring composition comprising a quinophthalone dye represented by Formula (1) was used, excellent performance was exhibited in all items. In the present invention, a quinophthalone dye represented by Formula (2) in particular had very high solubility in various organic solvents (for example, ethyl lactate, etc., which has higher safety) including the cyclohexane used in the Examples, and was effective from the viewpoint of work safety and alleviation of workload.

(Comparative Dye 1)
  CI Solvent Yellow 162
(Comparative Dye 2)
  CI Solvent Yellow 82
(Comparative Dye 3)
  Specific example 64 described in JP-A-5-271567.

[Chemical structure: a quinophthalone derivative with CH₃CH₂CH₂CH₂— substituent, Br, OH, and —O—C(=O)—CH=CH₂ groups]

(Comparative Dye 4)
  Specific example 22 of the dye monomer described in JP-A-2007-147784.

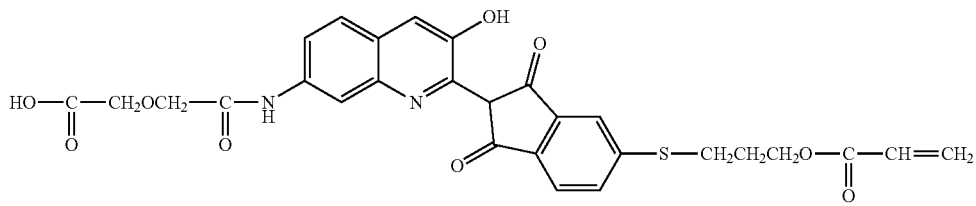

(Comparative Dye 5)

Specific example 39 of the dye monomer described in JP-A-2007-147784.

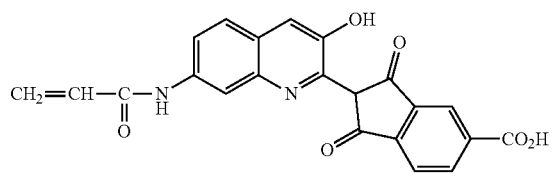 [SMILES: C=CC(=O)Nc1ccc2cc(O)c(C3C(=O)c4ccc(C(=O)O)cc4C3=O)nc2c1]

(Comparative Dye 6)

The carboxyl group-containing quinophthalone dye below without an ethylenically unsaturated group-containing substituent.

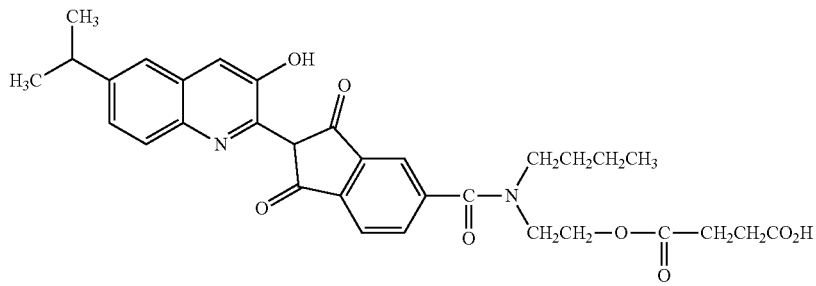

Example 11

—Preparation of Curable Coloring Composition (Positive-Working)—

A solution of a curable coloring composition (positive-working) was prepared by mixing and dissolving the components below.

| | |
|---|---|
| Ethyl lactate (EL) | 30 parts |
| Resin P-1 below | 3.0 parts |
| Naphthoquinone diazide compound N-1 below | 1.8 parts |
| Hexamethoxymethylolmelamine (crosslinking agent) | 0.6 parts |
| TAZ-107 (photo-acid generator, Midori Kagaku Co., Ltd.) | 1.2 parts |
| F-475 (fluorine-based surfactant, Dainippon Ink and Chemicals, Incorporated) | 0.0005 parts |
| Example compound (1) as dye related to the present invention | 1.5 parts |

—Synthesis of Resin P-1—

A three-necked flask was charged with 70.0 g of benzyl methacrylate, 13.0 g of methacrylic acid, 17.0 g of 2-hydroxyethyl methacrylate, and 600 g of 2-methoxypropanol and equipped with a stirrer, a reflux condenser, and a thermometer, and stirring was carried out under a flow of nitrogen at 65° C. for 10 hours with a catalytic amount of V-65 polymerization initiator (Wako Pure Chemical Industries, Ltd.) added. The resin solution thus obtained was added dropwise to 20 L of ion-exchanged water while vigorously stirring, thus giving a white powder. This white powder was vacuum dried at 40° C. for 24 hours, thus giving 145 g of resin PX. The molecular weight thereof was measured by GPC, and it was found that the weight-average molecular weight Mw was 28,000 and the number-average molecular weight Mn was 11,000.

—Synthesis of Naphthoquinone Diazide Compound N-1—

A three-necked flask was charged with 42.45 g of TrisP-PA (Honshu Chemical Industry Co., Ltd.), 61.80 g of o-naphthoquinone diazide-5-sulfonyl chloride, and 300 mL of acetone, and 24.44 g of triethylamine was added dropwise at room temperature over 1 hour. After the dropwise addition was completed, stirring was carried out for a further 2 hours, and a large amount of water was then poured into the reaction mixture while stirring. The precipitated naphthoquinone diazide sulfonic acid ester was collected by suction filtration and vacuum dried at 40° C. for 24 hours, thus giving photosensitive naphthoquinone azide compound N-1.

—Exposure and Development (Image Formation) of Curable Coloring Composition—

An undercoat layer-equipped glass substrate was prepared in the same manner as in Example 2, the undercoat layer-equipped glass substrate was coated with the curable coloring composition prepared above and pre-baked, exposed, developed, rinsed, and spray dried in the same manner as in Example 1, thus giving a pattern, and subsequently this pattern was heated at 180° C. for 5 minutes (post-baking). The cyan pattern thus formed showed a good profile with a rectangular shape.

Subsequently, the storage stability of the dye resist solution prepared above, and the heat fastness and light fastness of a coated film provided on a glass substrate using the dye resist solution were evaluated in the same manner as in Example 1, and in the same manner as for the above-mentioned negative-working system the storage stability, light fastness, and heat fastness were all good.

Examples 12 to 18

A coated film was provided on a silicon wafer substrate by the same procedure as in Examples 1 to 10 except that the glass substrate of Examples 1 to 10 was changed to the silicon wafer substrate. Subsequently, exposure was carried out using i-ray reduction projection exposure equipment at an exposure of 200 mJ/cm² to give a 1.2 μm square pattern, and development was carried out at 23° C. for 60 seconds using a developer formed by diluting CD-2000 (FUJIFILM Electronic Materials Co., Ltd.) to 60%. Subsequently, rinsing was carried out under running water for 30 seconds followed by spray drying. In accordance with the above, a pattern suitable as a color filter for a CCD having a good profile with a cross-section of the square pattern being substantially rectangular was obtained.

Industrial Applicability

In accordance with the present invention, there can be provided a curable coloring composition comprising a specific quinophthalone dye. Furthermore, in accordance with the present invention, there can also be provided a color filter that is compatible with a fine thin layer and a method for producing same. Because of this, the present invention can be suitably applied to full color recording with high image quality, etc.

What is claimed is:

1. A curable coloring composition comprising at least one quinophthalone dye represented by Formula (1) below,

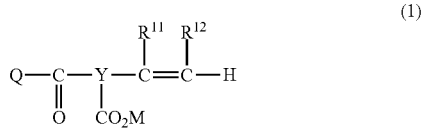

(1)

wherein $R^{11}$ and $R^{12}$ mutually independently denote a hydrogen atom, a substituted or unsubstituted alkyl group, or a substituted or unsubstituted aryl group, M denotes a hydrogen atom, lithium, sodium, potassium, or an ammonium, Y denotes a trivalent linking group represented by (Y-1) or (Y-2) below, and Q denotes a dye residue formed by removing one hydrogen atom from any possible position of a dye represented by Formula (Q) below,

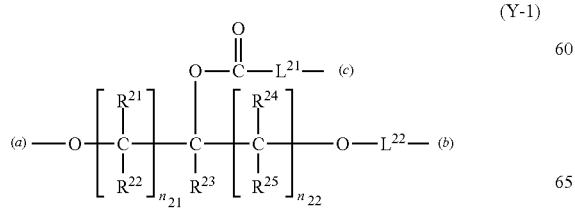

(Y-1)

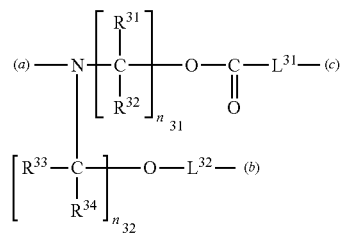

(Y-2)

wherein $R^{21}$, $R^{22}$, $R^{23}$, $R^{24}$, $R^{25}$, $R^{31}$, $R^{32}$, $R^{33}$, and $R^{34}$ mutually independently denote a hydrogen atom, a substituted or unsubstituted alkyl group, a substituted or unsubstituted aryl group, or a substituted or unsubstituted heterocyclic group, $n_{21}$ and $n_{22}$ mutually independently denote an integer of 0 to 3, $n_{31}$ and $n_{32}$ mutually independently denote an integer of 1 to 6, $n_{33}$ denotes an integer of 0 or 1, $L^{21}$ and $L^{31}$ denote a divalent linking group selected from the group consisting of (L-1) to (L-4) below, $L^{22}$ and $L^{32}$ denote a single bond or a divalent linking group selected from the group consisting of (L-4) to (L-7) below, (a) denotes a linking site to a carbonyl group bonded to dye residue (Q), (b) denotes a linking site to an ethylenically unsaturated group represented by $CR^{11}=CHR^{12}$, and (c) denotes a linking site to a carboxyl group represented by $CO_2M$,

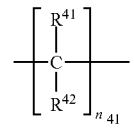

(L-1)

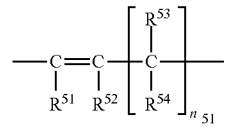

(L-2)

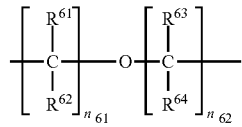

(L-3)

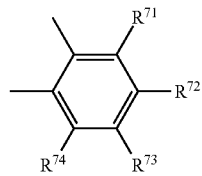

(L-4)

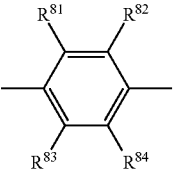

(L-5)

-continued

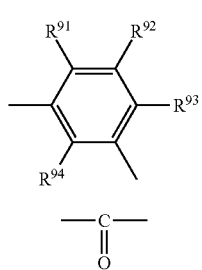
(L-6)

—C—
‖
O
(L-7)

wherein $n_{41}$, $n_{51}$, $n_{61}$ and $n_{62}$ mutually independently denote an integer of 1 to 3, and $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ mutually independently denote a hydrogen atom or a monovalent substituent, and when at least two of $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ are on the same carbon or at adjacent positions, they may be bonded to each other to form a 5- to 6-membered ring, and the ring may further have a substituent; in (L-1) to (L-4), a residue formed by removing $L^{21}$ from (Y-1) or a residue formed by removing $L^{31}$ from (Y-2) and a carboxyl group represented by $CO_2M$ may be bonded to either side, and in (L-4) to (L-7), a residue formed by removing $L^{22}$ from (Y-1) or a residue formed by removing $L^{32}$ from (Y-2) and an ethylenically unsaturated group represented by $CR^{11}{=}CHR^{12}$ may be bonded to either side, and (Q)

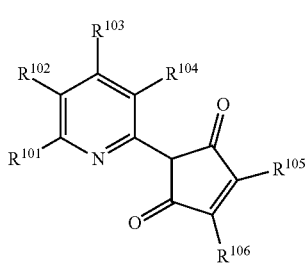

wherein $R^{101}$, $R^{102}$, $R^{103}$, $R^{104}$, $R^{105}$, and $R^{106}$ mutually independently denote a hydrogen atom or a monovalent substituent, and when at least two of $R^{101}$, $R^{102}$, $R^{103}$, $R^{104}$, $R^{105}$ and $R^{106}$ are at adjacent positions, they may be bonded to each other to form a 5- to 6-membered ring, and the ring may further have a substituent.

2. The curable coloring composition according to claim 1, wherein the curable coloring composition further comprises a polymerizable monomer.

3. The curable coloring composition according to claim 1, wherein the quinophthalone dye represented by Formula (1) above is a quinophthalone dye represented by Formula (2), (2)

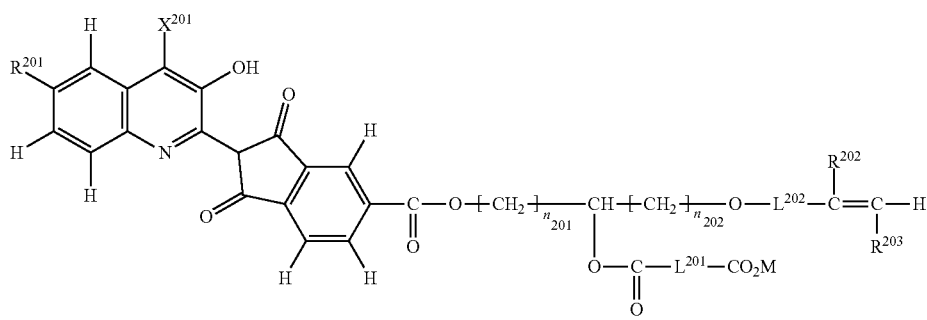

wherein $X^{201}$ denotes a hydrogen atom or a halogen atom, $R^{201}$ denotes a hydrogen atom or a substituted or unsubstituted alkyl group, $R^{202}$ and $R^{203}$ mutually independently denote a hydrogen atom, a substituted or unsubstituted alkyl group, or a substituted or unsubstituted aryl group, M denotes a hydrogen atom, lithium, sodium, potassium, or an ammonium, $L^{201}$ denotes a divalent linking group selected from the group consisting of (L-1) to (L-4) below, $L^{202}$ denotes a divalent linking group selected from the group consisting of (L-4) to (L-7) below, $n_{201}$ denotes an integer of 0 to 2, and $n_{202}$ denotes an integer of 1 or 2,

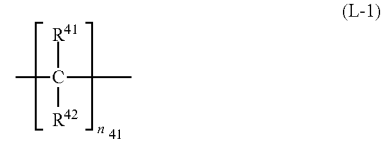
(L-1)

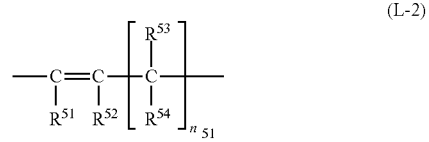
(L-2)

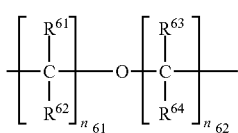 (L-3)

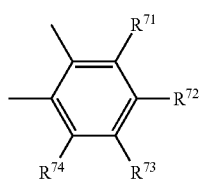 (L-4)

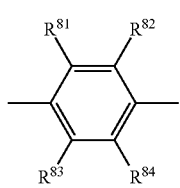 (L-5)

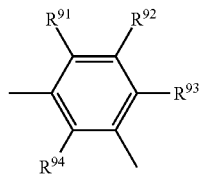 (L-6)

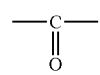 (L-7)

wherein $n_{41}$, $n_{51}$, $n_{61}$, and $n_{62}$ mutually independently denote an integer of 1 to 3, and $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ mutually independently denote a hydrogen atom or a monovalent substituent, and when at least two of $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ are on the same carbon or at adjacent positions, they may be bonded to each other to form a 5- to 6-membered ring, and the ring may further have a substituent; in (L-1) to (L-4), a residue formed by removing $L^{201}$-$CO_2M$ from Formula (2) and a carboxyl group represented by $CO_2M$ may be bonded to either side, and in (L-4) to (L-7), a residue formed by removing $L^{202}$-$CR^{202}$=$CHR^{203}$ from Formula (2) and an ethylenically unsaturated group represented by $CR^{202}$=$CHR^{203}$ may be bonded to either side.

4. The curable coloring composition according to claim 3, wherein $X^{201}$ is a hydrogen atom, a chlorine atom, or a bromine atom.

5. The curable coloring composition according to claim 3, wherein $R^{201}$ is a hydrogen atom or an alkyl group having 1 to 6 carbons.

6. The curable coloring composition according to claim 3, wherein the quinophthalone dye represented by Formula (2) above is a quinophthalone dye represented by Formula (2'),

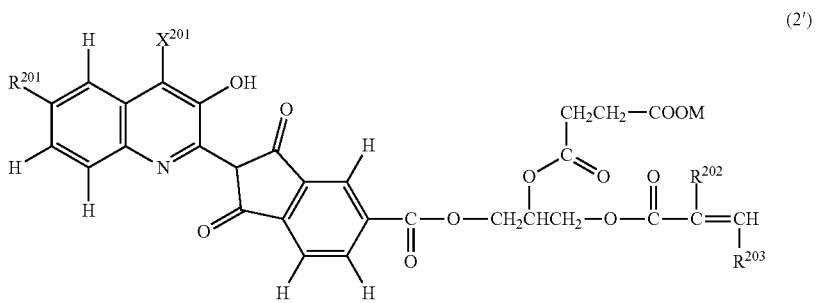

(2')

wherein $X^{201}$ denotes a hydrogen atom or a halogen atom, $R^{201}$ denotes a hydrogen atom or a substituted or unsubstituted alkyl group, $R^{202}$ and $R^{203}$ mutually independently denote a hydrogen atom, a substituted or unsubstituted alkyl group, or a substituted or unsubstituted aryl group, and M denotes a hydrogen atom, lithium, sodium, potassium, or an ammonium.

7. A method for producing a color filter comprising a step of forming a pattern image by coating a support with the curable coloring composition according to claim 1, imagewise exposing, and developing.

8. A color filter obtained by the production method according to claim 7.

9. A quinophthalone dye represented by Formula (2),

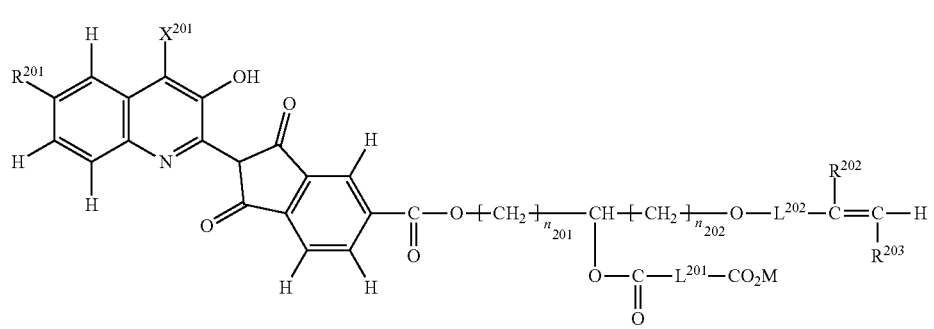

(2)

wherein $X^{201}$ denotes a hydrogen atom or a halogen atom, $R^{201}$ denotes a hydrogen atom or a substituted or unsubstituted alkyl group, $R^{202}$ and $R^{203}$ mutually independently denote a hydrogen atom, a substituted or unsubstituted alkyl group, or a substituted or unsubstituted aryl group, M denotes a hydrogen atom, lithium, sodium, potassium, or an ammonium, $L^{201}$ denotes a divalent linking group selected from the group consisting of (L-1) to (L-4) below, $L^{202}$ denotes a divalent linking group selected from the group consisting of (L-4) to (L-7) below, $n^{201}$ denotes an integer of 0 to 2, and $n^{202}$ denotes an integer of or 2,

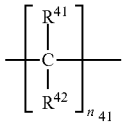 (L-1)

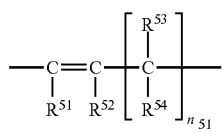 (L-2)

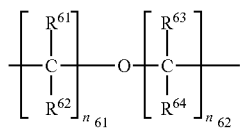 (L-3)

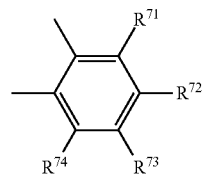 (L-4)

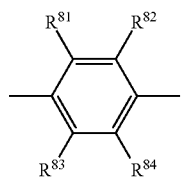 (L-5)

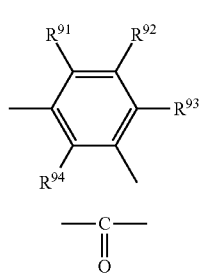 (L-6)

$$-\underset{\underset{O}{\|}}{C}-$$ (L-7)

wherein $n_{41}$, $n_{51}$, $n_{61}$, and $n_{62}$ mutually independently denote an integer of 1 to 3, and $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ mutually independently denote a hydrogen atom or a monovalent substituent, and when at least two of $R^{41}$, $R^{42}$, $R^{51}$, $R^{52}$, $R^{53}$, $R^{54}$, $R^{61}$, $R^{62}$, $R^{63}$, $R^{64}$, $R^{71}$, $R^{72}$, $R^{73}$, $R^{74}$, $R^{81}$, $R^{82}$, $R^{83}$, $R^{84}$, $R^{91}$, $R^{92}$, $R^{93}$, and $R^{94}$ are on the same carbon or at adjacent positions, they may be bonded to each other to form a 5- to 6-membered ring, and the ring may further have a substituent; in (L-1) to (L-4), a residue formed by removing $L^{201}$-$CO_2M$ from Formula (2) and a carboxyl group represented by $CO_2M$ may be bonded to either side, and in (L-4) to (L-7), a residue formed by removing $L^{202}$-$CR^{202}$=$CHR^{203}$ from Formula (2) and an ethylenically unsaturated group represented by $CR^{202}$=$CHR^{203}$ may be bonded to either side.

10. The quinophthalone dye according to claim 9, wherein $X^{201}$ is a hydrogen atom, a chlorine atom, or a bromine atom.

11. The quinophthalone dye according to claim 9, wherein $R^{201}$ is a hydrogen atom or an alkyl group having 1 to 6 carbons.

12. The quinophthalone dye according to claim 9, wherein the quinophthalone dye represented by Formula (2) above is a quinophthalone dye represented by Formula (2'),

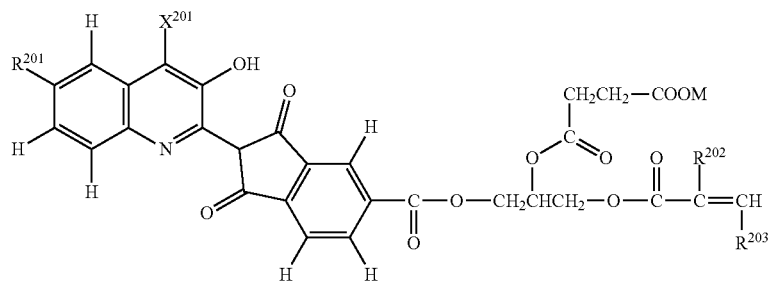
(2')
wherein $X^{201}$ denotes a hydrogen atom or a halogen atom, $R^{201}$ denotes a hydrogen atom or a substituted or unsubstituted alkyl group, $R^{202}$ and $R^{203}$ mutually independently denote a hydrogen atom, a substituted or unsubstituted alkyl group, or a substituted or unsubstituted aryl group, and M denotes a hydrogen atom, lithium, sodium, potassium, or an ammonium.
* * * * *